US006365730B1

(12) United States Patent
Jennings et al.

(10) Patent No.: US 6,365,730 B1
(45) Date of Patent: *Apr. 2, 2002

(54) DNA-ARMED RIBOZYMES AND MINIZYMES

(75) Inventors: Philip Anthony Jennings, Chatswood West; Maxine June McCall, Gladesville; Philip Hendry, Rozelle, all of (AU)

(73) Assignee: Gene Shears Pty. Limited, Neutral Bay (AU)

( * ) Notice: Subject to any disclaimer, the term of this patent is extended or adjusted under 35 U.S.C. 154(b) by 0 days.

This patent is subject to a terminal disclaimer.

(21) Appl. No.: 07/986,776

(22) Filed: Dec. 8, 1992

Related U.S. Application Data

(63) Continuation-in-part of application No. 07/717,602, filed on Jun. 19, 1991, now Pat. No. 5,298,612.

(30) Foreign Application Priority Data

Jun. 19, 1990 (AU) ............................................. PK0679
Dec. 21, 1990 (AU) ............................................. PK4002

(51) Int. Cl.$^7$ ........................... C07H 21/04; C12Q 1/68
(52) U.S. Cl. .................. 536/24.5; 536/23.1; 536/23.2; 435/6; 435/91.31; 435/375
(58) Field of Search ...................... 435/6, 91.31, 91.21, 435/91.1, 172.3, 320.1, 375; 536/23.2, 24.5; 514/44

(56) References Cited

U.S. PATENT DOCUMENTS

| 4,511,713 A | 4/1985 | Miller et al. .................... 435/6 |
| 4,987,071 A | 1/1991 | Cech ........................ 435/91.31 |
| 5,023,243 A | 6/1991 | Tullis et al. .................... 514/44 |
| 5,144,019 A | * 9/1992 | Rossi et al. ..................... 536/27 |
| 5,149,796 A | 9/1992 | Rossi ......................... 536/23.2 |
| 5,298,612 A | * 3/1994 | Jennings et al. ............ 536/23.2 |
| 5,972,701 A | 10/1999 | Jennings |
| 6,001,989 A | 12/1999 | Jennings |
| 6,008,343 A | 12/1999 | Jennings |
| 6,083,744 A | 7/2000 | Jennings |

OTHER PUBLICATIONS

Branch TIBS—Feb. 1998 pp. 45–50.*
Olsen et al. Biochemistry 30: 9735–9741, 1991.*
Odai et al. FEBS 267: 150–152, Jul. 1990.*
Pieken et al. Science 253:314–317, Jul. 1991.*
Stull et al. Pharm. Res. 12:465–483 (1995).*
Cameson et al. PNAS 86:9139–9143 (1989).*
Boehm, S., (1987) FEBS Letter 220:283–287 (Ex. 8).
Bruening, G. (1989) Methods of Enzym. 180:546–558 (Ex. 9).
Cech, T.R. (1987) Science 236:1532–1539 (Ex. 10).
Chuat, J., et al. (1989) Biochem. & Biophys. Res. Comm. 162:1025–1029 (Exhibit 12).
Cotten, M., et al. (1989) The EMBO Journal 8:3861–3866 (Ex. 13).
Dahm, S.C., et al. (1990) Biochimie 72:819–823 (Ex. 14).
Eckner, R. et al., (1991) The EMBO Journ. 10:3513–3522 (Ex. 15).
Forster, A.C. et al. (1988) NAture 334:265–267 (Ex. 16).
Goodchild, J., et al. (1991) Archives to Biochem & Biophys. 284(2):386–391 (Ex. 18).
Goodchild, J. et al. (1990) Poster No. 12 at Conf in San Diego(Ex.
Haseloff, et al. (1988) Nature 334:585–591 (Ex. 19).
Huillier, A. et al. Abstract from Conf. proceedings (Ex. 20).
Hutchins, C.J. et al. (1986) Nucleic Acids Research 14:3627=3635 (Exhibit 21).
Jefferies, A.C., et al. (1989) Nucl. Acids Res. 17:1371–1377 (Exhibit 22).
Kikuchi, Y., et al., (1991) Nucleic Acids Res. 19:6715–6755 (Ex. 2.
Koizumi, et al., (1988) FEBS Letters 228:228–230 (Ex. 24).
Koizumi, et al. (1989) Nucleic Acids Res. 17:7059–7071 (Ex. 25).
Lamb, J.W., et al. (1990) J. Gen. Virol. 71:2257–2264 (Ex. 26).
McClain et al. (1987) Science 238:527–530 (Ex. 27).
Miller et al. (1991) Virology 183:711–720 (Ex. 28).
Perreault, J–P, et al. (1991) Biochem. 30:4020–4025 (Ex. 29).
Ruffner, D.E. et al. (1989) Gene 82:31–41 (Ex. 30).
Ruffner, D.E. et al. (1990) Biochemistry 29:10695–10702 (Ex. 31).
Sampson, et al. (1987) Cold Spring Harbor Sym Quant. Biol. 52:267–275 (Exhibit 32).
Sarver, et al. (1990) Science 247:1222–1224 (Exhibit 33).
Saxena, et al. (1990) J. Biol. Chem. 265:17106–17109 (Ex. 4).
Scanlon, K. et al. (1991) Proc. Natl. Acad. Sci. 88:10591–10595 (Exhibit 34).
Sheldon, C.C. et al. (1989) Nucleic Acids Res. 17:5665–5678 (Ex. 35.
Symons, R.H. (1989) Tibs, 14:445–450 (Exhibit 36).
Tabler, M. et al. (1991) Gene 108:175–183 (Exhibit 37).
Uhlenbeck, et al. (1987) Nature 328:596–600 (Ex. 38).
Yang, et al. (1990) Biochemistry 29:11156–11160 (Ex. 39).
Zaug, et al. (1986 A) Science, 231:473–474 (Exhibit 40).
Zaug, et al. (1986 B) Nature 234:429–433 (Exhibit 41).
Perreault et al. (1990) Nature, 344:565–567.
Forster et al. (1987) Cell 50:9–16.
Uhlmann et al. (1990) Chem. Revs. 90:544–584.

* cited by examiner

*Primary Examiner*—Andrew Wang
(74) *Attorney, Agent, or Firm*—John P. White; Cooper & Dunham LLP

(57) ABSTRACT

The invention describes catalytic nucleic acid based compounds capable of cleaving nucleic acid polymers both in vivo and in vitro. Two embodiments of this invention are compounds with a short stem that does not base pair, a minizyme, and compounds with DNA hybridizing arms and RNA catalytic domain and stem, DNA-armed ribozymes. The compounds of this invention, while nucleotide based may be substituted or modified in the sugar, phosphate, or base. Methods of use and methods of treatment are also described.

29 Claims, 15 Drawing Sheets

FIGURE 11

```
3' aggtccttC   tcggatcctg 5'
         A    CUG
         A       A
         A    GU
         G   A
          C·G
          G·C
          U   U
           UU
```
TATRB-H2

```
3' aggtccttC   tcggatcctg 5'
         A    CUG
         A       A
         A    GU
         G   A
          C·G
          A·U
          G·C
          G·C
          U   U
           UU
```
TATRB-H4

```
3' aggtccttC   tcggatcctg 5'
         A    CUG
         A       A
         A    GU
         G   A
          C·G
          A·U
          G·C
          G·C
          C·G
          A·U
          G·C
          G·C
          U   U
           UU
```
TATRB-H8

FIGURE 14

```
3'    aggtccttCA      tcggatcctg 5'
              A      CUG
              A         A
              G      AGU
                C-G
                A-U
                G-C
                G-C
                U   U
                 UU
```

TAT RG (RNA arms and DNA helix II)
```
3'  AGGUCCUUCA      UCGGAUCCUG 5'
              A      CUG
              A         A
              G      AGU
                c-g
                a-t
                c-g
                c-g
                t   t
                 tt
```

TAT RH (mixture of DNA and RNA in arms and helix II/linker)
```
3'    aggtcCUUCA      UCGGAtcctg 5'
              A      CUG
              A         A
              G      AGU
                C-G
                A-U
                G-C
                G-C
                t   t
                 tt
```

DNA-ARMED RIBOZYMES AND MINIZYMES

This application is a continuation-in-part of U.S. Ser. No. 717,602, filed Jun. 19, 1991, now U.S. Pat. No. 5,298,612.

BACKGROUND OF THE INVENTION

Throughout this application various publications are referred to by author and year within brackets. The full references are listed alphabetically after the Experimental Section. The disclosures for these publications in their entireties are hereby incorporated by reference into this application to more fully describe the state of the art to which this invention pertains.

Ribozymes are RNA molecules that can cut or ligate other nucleic-acid molecules (usually RNA) in a catalytic fashion (Cech and Bass, 1986; Altman, et al., 1987). The hammerhead ribozyme is one of the best-known ribozymes. It has been studied extensively in isolated chemical systems (Forster and Symons, 1987; Uhlenbeck, 1987; Haseloff and Gerlach, 1988; Jeffries and Symons, 1989; Koizumi, et al., 1988), and used in gene-control studies in living cells (Cotten and Birnstiel, 1989; Cameron and Jennings, 1989; Sarver, et al., 1990; Saxena and Ackerman, 1990; Sioud and Drlica, 1991; Sioud, et al., 1992). A hammerhead ribozyme as defined by Haseloff and Gerlach (Haseloff and Gerlach, 1988) is shown in FIG. 1. It contains two stretches of conserved nucleotides (boxed), a stem-loop structure (bases 18–29) containing helix II, and flanking nucleotides which form double-helices I and III in combination with the substrate.

The instability of ribozymes in living cells is a major concern. One approach taken to protect transcribed ribozymes from nuclease attack in cells has been to embed the ribozyme in a larger, folded structure. Thus, hammerhead ribozymes have been placed next to the anti-codon loop in t-RNA$^{met}$ (Cotten and Birnstiel, 1989), the 3' untranslated region of the luciferase gene (Cameron and Jennings, 1989), and in a molecule with bacteriophage T7 transcription terminator at its 3' end (Sioud, et al, 1992). These ribozymes appeared to be more stable than the corresponding, unprotected ribozymes; however, in the only comparative study, the stabilized ribozyme did not cleave more target RNA than the shorter-lived ribozyme, indicating that the protecting structure may decrease the specific activity of that ribozyme (Sioud, et al., 1992).

An alternative approach has been to chemically synthesize ribozymes with ribonucleotides modified at the 2' position. The modified nucleotides have included 2'-deoxy-, 2'fluoro-, 2'-amino-, 2'-O-allyl- and 2'-O-methyl-ribonucleotides (Perreault, et al., 1990; Perreault, et al., 1991; Olsen, et al., 1991; Pieken, et al., 1991; Williams, et al., 1992; Paolella, et al., 1992). A ribozyme consisting predominantly of 2'-O-allyl ribonucleotides displayed greatly improved stability compared to an unmodified ribozyme in the presence of bovine serum (Paolella, et al., 1992). Modifications to nucleotides in the hybridizing arms and/or in helix II of the ribozyme have little effect on catalytic efficiency (Olsen, et al., 1991; Pieken, et al., 1991; Williams, et al., 1992; Paolella, et al., 1992); for example, substitution of the 2'-hydroxyl groups with 2'-O-allyl groups in all non-conserved nucleotides of a hammerhead ribozyme resulted in full retention of activity (Paolella, et al., 1992). On the other hand, changing the 2'-substituent in any of the conserved nucleotides of the ribozyme resulted in a decrease in catalytic activity, the magnitude of which varied greatly depending on the number of changes, the nature of the change, and the particular nucleotides modified (Perreault, et al., 1990; Perreault, et al., 1991; Olsen, et al., 1991; Pieken, et al., 1991; Williams, et al., 1992; Paolella, et al., 1992).

SUMMARY OF THE INVENTION

The invention describes catalytic nucleic acid based compounds capable of cleaving nucleic acid polymers both in vivo and in vitro. Two embodiments of this invention are compounds with a short stem that does not base pair, a minizyme, and compounds with DNA hybridizing arms and RNA catalytic domain and stem, DNA-armed ribozymes. The compounds of this invention, while nucleotide based may be substituted or modified in the sugar, phosphate, or base. Methods of use and methods of treatment are also described.

BRIEF DESCRIPTION OF THE FIGURES

FIG. 11. The figure shows the structure of three DNA-armed ribozymes with varying stem length TATRB-H2, TATRB-H4, TATRB-8(SEQ ID NO:13–15).

FIG. 14. The structure of three ribozymes targeted against a TAT substrate. The first ribozyme has had the phosphates replaced by phosphothiolates in the stem loop of helix II (capital letter in italics) and DNA arms(TAT RBPS). The second ribozyme has RNA arms and a DNA stem (TAT RG) and the third ribozyme has mixed RNA DNA arms and stem (TAT RH) (SEQ ID NO:16–18).

DETAILED DESCRIPTION OF THE INVENTION

Figure 1:
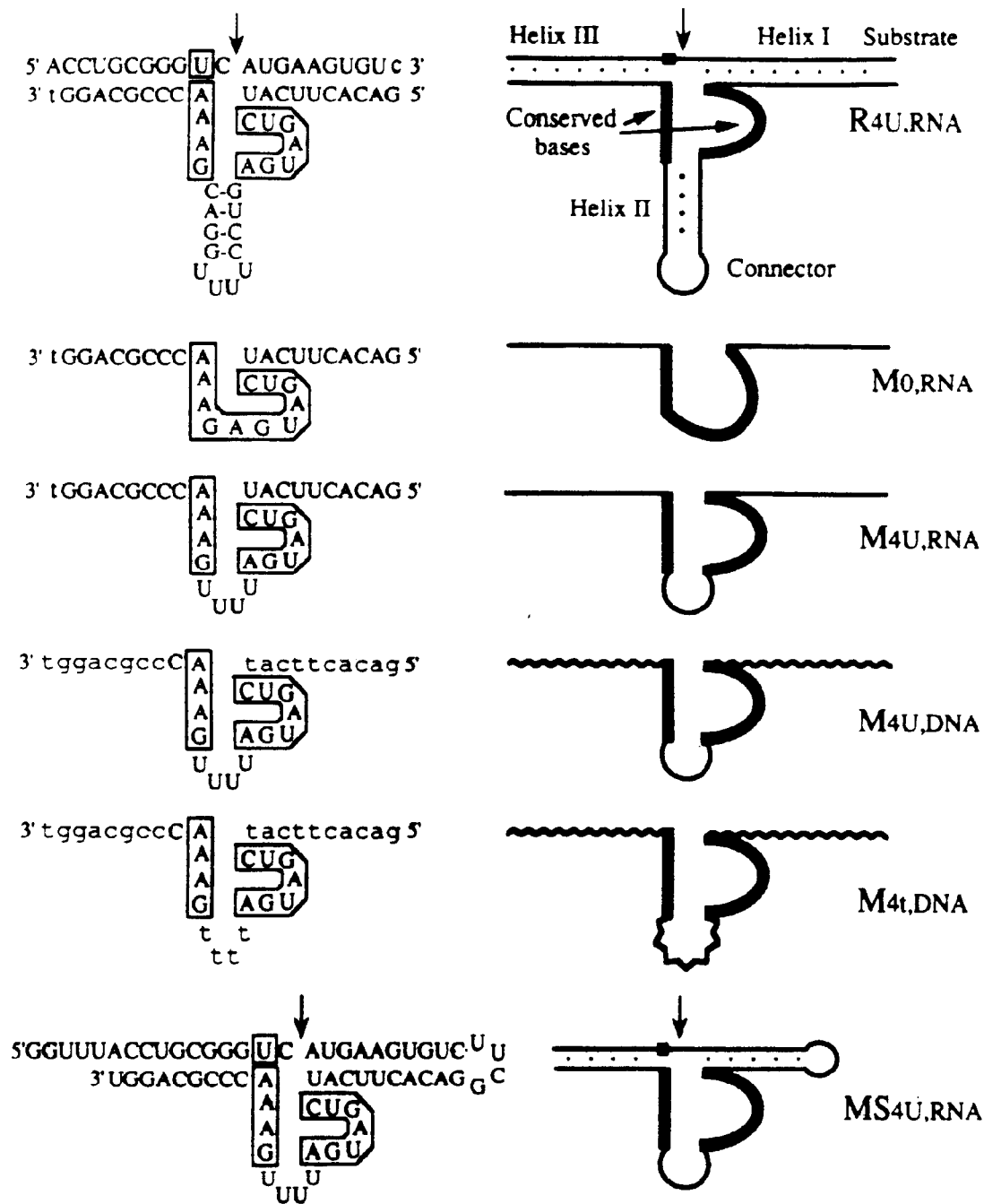
FIG. 1. Base sequence, schematic representation, and names of ribozyme, minizymes, and their common substrate. Conserved ribonucleotides are drawn in boxes and depicted schematically by thick lines, other ribonucleotides are depicted by uppercase letters and thin lines, and deoxyribonucleotide are depicted by lowercase letters and wavy lines. R, ribozyme containing helix II; M, minizyme not containing helix II; MS, a minizyme and substrate in the same molecule; the first subscript indicates the bases in the connector, and the second subscript indicates whether RNA or DNA nucleotides are in the flanking arms that form helices I and II with the substrate. The ribozyme and minizymes cleave the substrate after the cytidine residue marked by a downward arrow(SEQ ID NO:1–7).

The ribozyme which has been stabilized against intracellular degradation needs to be reasonably active. In the course of our work on reducing the size and RNA-content of the hammerhead ribozyme, we produced a minimized ribozyme in which the stem-loop of helix II was replaced by four ribonucleotides (McCall, et al., 1992). This 'minizyme' was less active, at cleaving a synthetic substrate of 21 nucleotides, than its parent ribozyme which contained a helix II. However, the cleavage activity of the minizyme increased unexpectedly, when the RNA nucleotides in the hybridizing arms of the minizyme were replaced by DNA (McCall, et al., 1992). Further, minizymes were more active than ribozymes against a long substrate vide infra.

Ribozymes are RNAs capable of catalyzing RNA cleavage reactions. One simplest and most commonly used are the hammerhead type ribozymes which contain a conserved catalytic domain and flanking sequences that hybridize with the substrate RNA (Haseloff et al. PCT International Publication No WO 89/05852). Hammerhead ribozymes can be targeted against any RNA sequence that contain an XUX triplet amenable for cleavage. Several studies have demonstrated the ability of these ribozymes to cleave a target RNA in vivo and suppress protein expression. Other classes of ribozymes are tetrahymena IVS (Group I Intron) (Cech et al. U.S. Pat. No. 4,740,463), RNAse P (Altman et al. PCT International Publication No WO 92/03566), and hairpin ribozymes (Hampel et al., 1990). Further, hammerhead compounds with DNA arms, DNA stem loops, and RNA catalytic region have been described subsequent to applicants effective filing date (Rossi et al., U.S. Pat. No. 5,144, 019).

One embodiment of the invention is a minizyme, a compound having the structure:

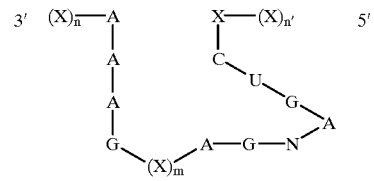

wherein each X is the same or different and represents a ribonucleotide or a deoxyribonucleotide which may be modified or substituted in its sugar, phosphate or base; wherein (X)$_n$ and (X)$_{n'}$ represent oligonucleotides in which n and n' are integers which define the number of nucleotides in the oligonucleotides, such oligonucleotides having predetermined sequences sufficiently complementary to a predefined RNA target sequence to be cleaved to allow hybridization to the RNA target sequence. In one embodiment of the structure above 3' (X)$_n$—A is 3' (X)$_{n-1}$—CA. N may be adenine, guanine, cytosine, or uracil, but preferably cytosine or uracil. In the structure above each solid line represents a chemical linkage providing covalent bonds between the nucleotides located on either side thereof and m represents an integer from 2 to 20. Preferably, the number of nucleotides in the (X)$_m$ is from 2 to 6. In this embodiment of the invention none of the nucleotides (X)$_m$ are Watson-Crick base paired to each other or other nucleotide within the compound.

In one embodiment of the invention the compound is entirely composed of RNA. In another embodiment, the hybridizing arms (X)$_n$ and stem (X)$_m$ are composed of DNA.

The absence of base pairing is an advantageous feature of this invention as endonucleases comprising a minimal number of nucleotides may be produced according to standard methods described herein. The applicants have surprisingly discovered that base pairs between nucleotides in the group $(X)_m$ are not required to permit the endonuclease of this invention to cleave its target substrate. Accordingly, the group $(X)_m$ may comprise any number of non base paired nucleotides, for example, two nucleotides (such as TT), four nucleotides (such as AAAA, UUUU, TTTT, etc.) or five nucleotides (such as TTTTT). The nucleotide sequence of the group $(X)_m$ under these circumstances is not of importance and the number of nucleotides is also not of importance. The main consideration to take into account is that the resultant endonuclease is capable of substrate cleavage. This can be readily measured without undue experimentation in standard cleavage assays on an appropriate target nucleotide sequences as described herein.

Another embodiment of the invention is a DNA-armed ribozyme, a compound having the structure:

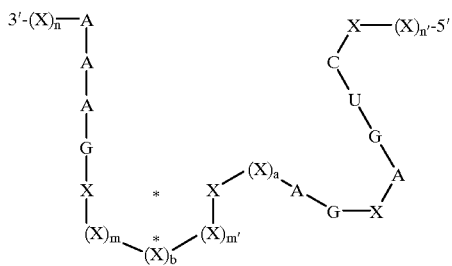

wherein each X represents a ribonucleotide which is the same or different and may be modified or substituted in its sugar, phosphate or base; wherein each x (lower case) represents a deoxyribonucleotide which is the same or different and may be modified or substituted in its sugar, phosphate or base. Each of A, C, U, and G represents a ribonucleotide which may be unmodified or modified or substituted in its sugar, phosphate or base. Each of $(x)_n$ and $(x)_{n'}$ represents an oligodeoxyribonucleotide having a predetermined sequence and each of n and n' represents an integer which defines the number of deoxyribonucleotides in the oligonucleotide with the proviso that the sum of n+n' is sufficient to allow the compound to hybridize with the RNA target sequence. In one embodiment, 3' $(x)_n$—A is 3' $(x)_{n-1}$—CA. In some instances it will be desirable to have the hybridizing arms exactly complementary to the target sequence it is not manditory. Each * represents base pairing between the nucleotides located on either side thereof. Preferably, the compound will have two or eight base pairs in the stem. Each solid line represents a chemical linkage providing covalent bonds between the ribonucleotides located on either side thereof. $(X)_a$ may be present or absent in the conserved region. Each of m and m' represents an integer which is greater than or equal to 1 but prefereably m is 1 or 7. $(X)_b$ represents an oligoribonucleotide and b represents an integer which is greater than or equal to 2. Preferably, $(X)_b$ contains 4 nucleotides.

Yet another embodiment of the invention is an endonuclease of the formula (I)

$$X—M—Y \qquad (I)$$

wherein X and Y represent nucleotide sequences comprised of deoxyribonucleotides, ribonucleotides, or combinations thereof or derivatives thereof; said nucleotide sequences being of sufficient length to allow hybridization to a target nucleic acid sequence desired to be cleaved by said endonuclease; and wherein M represents a catalytic region of the formula:

$$5'C^1U^2G^3A^4N^5G^6A^7—P—G^8A^9A^{10}A^{11}N^{12} \; 3' \qquad (II)$$

where A, G, C and U respectively represent bases adenine, guanine, cytosine and uracil which may be in the form of deoxyribonucleotides, ribonucleotides, or combinations thereof or derivatives thereof; and $N^{12}$ is selected from any of the bases adenine, guanine, cytosine, uracil or thymine, or derivatives thereof; and wherein P is one or more nucleotides, which nucleotides may be deoxyribonucleotides, ribonucleotides, or a combination of one or more deoxyribonucleotides and one or more ribonucleotides, or derivatives thereof, wherein if said nucleotides solely comprise ribonucleotides and the nucleotide sequences X and Y are solely comprised of ribonucleotides, then said ribonucleotides of the group P are not base paired to one another; or a bond or any atom or any group of interconnected atoms linking nucleotides $A^7$ and $G^8$, which does not destroy the cleavage capability of the catalytic region and which is not solely comprised of nucleotides.

The group P in formula (II) may comprise ribonucleotides, deoxyribonucleotides, or at least one deoxyribonucleotide and at least one ribonucleotide, or derivatives thereof wherein all nucleotides are base paired, or not all of the nucleotides are base paired. Complementary nucleotides in the nucleotide sequence P linking nucleotides $A^7$ and $G^8$ of the formula (II), may be base paired by Watson-Crick base pairs, Hoogsteen base pairs, or other base pairing known in the art. Where the nucleotide sequence of the group P is partly base paired (that is, not all nucleotides are base paired), there may be provided regions of base pairing and one or more single-stranded regions, for example, a base paired stem and a loop of non base paired nucleotides. For example, a stem and loop arrangement is described by Haseloff and Gerlach, supra.

Where P comprises a nucleotide sequence, the nucleotide sequence may comprise a ribonucleotide sequence or a combination of one or more ribonucleotides and one or more deoxyribonucleotides, in which none of these bases are paired, or at least one of the bases is base paired (i.e., this including where all of the bases are base paired, and where not all of the bases are paired). Alternatively, the group P may comprise a deoxyribonucleotide sequence in which none of the bases are paired or at least one of the bases are paired (again this including where all of the bases are base paired, and where not all of the bases are base paired).

The nucleotides of the groups X and Y may be of any length and sequence sufficient to enable hybridization formation with complementary nucleotides in the target RNA, as described herein. The nucleotides may be in the form of deoxyribo-nucleotides, ribonucleotides, deoxyribonucleotide ribonucleotide hybrids, or derivatives thereof as hereinbefore described. These flanking sequences may be chosen to optimize stability of the endonuclease from degradation. For example, deoxyribonucleotides are resistant to the action of ribonucleases. Modified bases, sugars or phosphate linkages of nucleotides, such as phosphoramidate, or phgosphorothioate linkages in the phosphate backbone of the nucleotide sequences, may also provide resistance to nuclease attack. Binding affinity may also be optimised in particular circumstances, by providing nucleotides solely in the form of ribonucleotides, deoxyribonucleotides, or combinations thereof. In some circumstances it may be necessary to optimise the composition of the groups X and Y, to maximize target RNA cleavage. The cleavage activity of endonucleases having flanking nucleotide sequences which hybridise to target sequences and which are comprised wholly of deoxyribonucleotides may, in some circumstances, have reduced activity. In such circumstances optimisation may involve providing a mixture of deoxyribonucleotides and ribonucleotides in the nucleotide sequences X and Y. For example, nucleotides in the endonuclease which are proximal to the cleavage site in a target RNA may be in the form of ribonucleotides. The nucleotides $A^{11}$ and $N^{12}$ of the formula (II) interact with the target sequence adjacent to the cleavage site, with $A^{11}$ interacting with the U of the target sequence X'UY', where X' and Y' are as herein defined. The nucleotide $N^{12}$ is selected to be complementary to the nucleotide represented by X'. These nucleotides, or nucleotides in a 5' direction may, for example, be in the form of ribonucleotides. Where a target sequence is shown to be relatively resistant to certain embodiments of endonucleases of this invention, it may be necessary to provide nucleotide sequences X and Y partly or wholly in the form of ribonucleotides. Where desired, protection from nuclease attack as will be hereinafter described.

The invention also encompasses poly minizymes or DNA-armed ribozymes or mixtures thereof e.g. compounds having the structure:

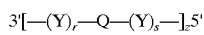

$$3'[-(Y)_r-Q-(Y)_s-]_z 5'$$

wherein Q represents a minizyme or DNA-armed ribozyme as described above which may be the same or different. Each Y represents a spacer, a ribonucleotide or a deoxyribonucleotide which is the same or different and may be modified or substituted in its sugar, phosphate or base. Each of r and s represents an integer which is greater than or equal to 0. z represents an integer from 1 to 100.

Poly-endonucleases have the potential to act as anti-sense molecules (Helene, C. and J-J Toulme (1990) Biochemica, Biophysica, Acta 1049: 99–125) as well as endonucleases. By "antisense" is meant the formation of a duplex or double stranded sequence as a result of base pairing between complementary bases of a target sequence and an antisense oligonucleotide, which prevents translation of said sequence as a result of duplex formation or the creation of a template for cleavage of the RNA by RNase H, a cellular ribonuclease which acts to cleave the RNA component of hybridized RNA and DNA sequences.

Ribonucleotide and deoxyribonucleotide derivatives or modifications are well known in the art, and are compatible with commercially available DNA synthesizers. (See Saenger, 1984, particularly pages 159–200). Nucleotides comprise a base, sugar and a monophosphate group. Accordingly, nucleotide derivatives, substitutions, or modifications may be made at the level of the base, sugar, or monophosphate.

A large number of modified bases are found in nature, and a wide range of modified bases have been synthetically produced (Saenger, 1984; and CRC Handbook of Biochemistry). Suitable bases would include inosine, 5'-methylcytosine, 5'-bromouracil, xanthine, hypoxanthine and other such bases. For example, amino groups and ring nitrogens may be alkylated, such as alkylation of ring nitrogen atoms or carbon atoms such as $N^1$ and $N^7$ of guanine and $C^5$ of cytosine; substitution of keto by thioketo groups; saturation of carbon=carbon double bonds, and introduction of a C-glycosyl link in pseudouridine. Examples of thioketo derivatives are 6-mercaptopurine and 6-mercaptoguanine.

Bases may be substituted with various groups, such as halogen, hydroxy, amine, alkyl, azido, nitro, phenyl and the like. Bases may be substituted with other chemical species, such as an amino-acid side chain or linkers which may or may not incorporate other chemical entities, e.g. acidic or basic groups. For example, guanine ($G_3$) may be substituted with tyrosine, and cytosine (C1) or adenine (A11) similarly substituted with histidine.

The sugar moiety of the nucleotide may also be modified according to well known methods in the art (Saenger, 1984). This invention embraces various modifications to the sugar moiety of nucleotides as long as such modifications do not abolish cleavage activity of the compound. Examples of modified sugars include replacement of secondary hydroxyl groups with halogen, amino or azido groups; 2'-methylation; conformational variants such as the $O_2$'-hydroxyl being cis-oriented to the glycosyl $C_1$. —N link to provide arabinonucleosides, and conformational isomers at carbon $C_1$, to give α-nucleosides, and the like. Further, non ribose sugars may be used such as hexoses such as glucose, pentoses such as arabinose.

The phosphate moiety of nucleosides is also subject to derivatisation or modifications, which are well known in the art. For example, replacement of oxygen with nitrogen, sulphur or carbon derivatives to respectively give phosphoramidates, phosphorothioates, phosphodithiolates, and phosphonates. Substitutions of oxygen with nitrogen, sulphur of carbon derivatives may be made in bridging or non bridging positions. It has been well established from work involving antisense oligonucleotides that phosphodiester and phosphorothioate derivatives may efficiently enter cells (particularly when of short length), possibly due to association with a cellular receptor. Methylphosphonates are probably readily taken up by cells by virtue of their electrical neutrality.

The phosphate moiety may be completely replaced with peptide nucleic acids (see Hanvey et al., 1992; Nielson, 1991; and Egholm, 1992). Other replacements are well-known to those skilled in the art for example siloxane bridges, carbonate bridges, acetamidate bridges, carbamate bridges, thioether bridges, etc. (Uhlmann and Peymann, 1990).

In the catalytic region, conserved region (see FIG. 1) nucleotide additions, deletions or replacements may be made as described above with the proviso that activity is not destroyed. For example, any one of the conserved nucleotides may be substituted with one or more ribo- and/or deoxyribonucleotides containing bases such as adenine, guanine, cytosine, methyl cytosine, uracil, thymine, xanthine, hypoxanthine, inosine, or other methylated bases.

As will be readily appreciated by workers in the field to which this invention relates, the cleavage of a target RNA may be readily assessed by various methods well known in the art (for example, see Sambrook et al., 1989). Cleavage may, for example, be assessed by running the reaction products (where the substrate is radioactively labelled) on acrylamide, agarose, or other gel systems, and then subjecting the gel to autoradiography or other analytical technique to detect cleavage fragments (Sambrook et al., 1989).

By way of example, blocking groups may be added from optionally substituted alkyl, optionally substituted phenyl, optionally substituted alkanoyl. Optional substituents may be selected from C1–C5 alkoxy and the like. Alternatively, nucleotide analogues such as phosphothioates, methylphosphonates or phosphoramidates or nucleoside derivatives (such as α-anomers of the ribose moiety), hexoses such as glucose, non-ribose pentoses such as arabinose, which are resistant to nuclease attack may be employed as terminal blocking groups.

Alternatively, non nucleic acid groups which alter the susceptibility of the endonuclease molecule to other nucleases may be inserted into the 3' and/or 5' end of the endonuclease. For example, 9-amino-acridine attached to the endonuclease may act as a terminal blocking group to generate resistance to nuclease attack on the endonuclease molecules and/or as an intercalating agent to aid endonucleolytic activity. It will be readily appreciated that a variety of other chemical groups, e.g. spermine or spermidine could be used in a related manner.

One or more ribonucleotides and/or deoxyribonucleotides of the group $(X)_m$ may be replaced, for example, with a linker selected from optionally substituted polyphosphodiester (such as poly (1-phospho-3-propanol)) optionally substituted alkyl, optionally substituted polyamide, optionally substituted glycol, and the like. Optional substituents are well known in the art, and include alkoxy (such as methoxy, ethoxy and propoxy), straight or branch chain lower alkyl (such as $C_1$–$C_5$ alkyl), amine, aminoalkyl (such as amino $C_1$–C5 alkyl), halogen (such as F, Cl and Br) and the like. The nature of optional substituents is not of importance, as long as the resultant endonuclease is capable of substrate cleavage.

Additionally, suitable linkers may comprise polycyclic molecules, such as those containing phenyl or cyclohexyl rings. Such compounds would generally comprise suitable functional groups to allow coupling through reactive groups on nucleotides.

Synthetic preparations of mRNA are well known (see Sambrook et al., 1989). Mixed DNA-RNA oligomers with modified base pairs for the ribozyme or minizyme can be prepared by commercially available DNA synthesizers such as those produced by Applied Biosystems, Biosearch, or Milligen (see, e.g., Perrault et al, 1990) for derivatives (Uhlmann, E. and Peyman, A., 1990), H-phosphonate monomers see (Agrawal et al U.S. Pat. No. 5,149,798).

The compounds of this invention may be covalently or non-covalently associated with affinity agents such as proteins, antibodies, steroids, hormones, lipids, specific nucleic acid sequences, intercalating molecules (such as acridine derivatives, for example 9-amino acridine) or the like to modify binding affinity for a substrate nucleotide sequence or increase affinity for target cells, or localization in cellular compartments or the like. For example, the compounds of the present invention may be associated with RNA binding peptides or proteins which may assist in bringing the endonuclease into juxtaposition with a target nucleic acid such that hybridization and cleavage of the target sequence may take place. Nucleotide sequences may be incorporated into the 5' and 3' ends of the groups $(X)_n$ and $(X)_n$, to increase affinity for substrates. Such additional nucleotide sequences may form triple helices with target sequences (Strobel, et al., 1991) which may enable interaction with intramolecularly folded substrate. Alternatively, modified bases vide supra within the additional nucleotide sequences may be used that will associate with either single stranded or duplex DNA generating base pair, triplet, or quadruplet, interactions with nucleotides in the substrate.

The compounds of the claimed invention may be further stabilized using methods in the literature for example the use transcription terminators on the 3' end such as the T7 terminator, ρ-independent terminator, cry element (Gelfand et al. U.S. Pat. No. 4,666,848) or the TrpE terminator. Furthermore, sequences such as the poly(A) addition signal AATAAA may be added and strategies involving changing the length of the 3' non-coding region (see Gillies, U.S. Pat. No. 5,149,635). These techniques can be used to stabilize RNA in the compound.

The invention also embodies methods of production of the RNA based compounds described above comprising the steps of: (a) ligating into a transfer vector comprised of DNA, RNA or a combination thereof a nucleotide sequence corresponding to said compound; (b) transcribing the nucleotide sequence of step (a) with RNA polymerase; and (c) recovering the compound. The invention also includes transfer vectors, bacterial or phage, comprised of RNA or DNA or a combination thereof containing a nucleotide sequence which on transcription gives rise to the compounds or RNA molecules described above.

The invention described herein also provides a method of cleavage of a specific RNA target sequence which comprises reacting a compound (e.g. minizyme, DNA-armed ribozyme, or polymer thereof) with the target sequence so as to thereby cleave the specific target sequence. Such target sequences may be indigenous to mammals or plants. Preferably, the target sequence is in a viral gene. The invention also provides a method for the treatment of viral diseases in plants and animals.

Further, many methods have been developed for introducing cloned eukaryotic DNAs into cultured mammalian cells (Sambrook et al., 1989):

Calcium phosphate- or DEAE-dextran-mediated transfection;

Polybrene;

Protoplast fusion;

Electroporation; and

Direct microinjection into nuclei.

Further, the compound described herein may be used in plants to cleave undesirable mRNA. The appropriate cleavage would lead to phenotypic changes. Phenotypic changes in plant cells or plants may include drought resistance, salinity resistance, resistance to fungal, viral or bacterial infection; modifications of growth characteristics; sterility; fruit production; flowering; senescence; altering oil seed metabolic pathways to increase production; and the like (see Shewmaker et al. U.S. Pat. No. 5,107,065). It is evident that one or more RNA involved in determining phenotype are identified, such RNAs may be inactivated by cleavage utilizing the endonuclease of this invention and thus the phenotype of the plant or plant cell altered. Diseases or infections which may be treated in plants with endonucleases of this invention include fungal infection, bacterial infections (such as Crown-Gall disease) and disease associated with plant viral infection.

Phenotypic modifications within animals (including in some applications man)which may be effected by cleaving and thus inactivating target RNAs associated with phenotype would include growth characteristics of animals, fertility, skin/cosmetic modifications, reproductive characteristics, disease resistance and the like. Myriad applications arise for phenotypic modifications in animals, and plants as previously mentioned. One or more RNAs associated with a given endonucleases may be targeted against such RNAs for their inactivation with consequential phenotypic modification.

Prokaryotic and eukaryotic cell cultures may be phenotypically modified by treatment with endonucleases of this invention. For example, bacterial cultures or yeast cultures involved in production of food components (such as cheese, bread and dairy products) and alcoholic beverage production may be treated so as to modify enzyme content, flavor production, cell growth rate, culture conditions and the like. Eukaryotic and prokaryotic cells in culture may, for example be protected from infection or disease associated with mycoplasma infection, phage infection, fungal infection and the like.

The compounds of this invention may also be used to treat diseases or infection in humans, animals, plants, or prokaryotic or eukaryotic cells. The ability to treat disease or infection is based on the fact that the compounds of this invention are capable of cleaving any RNA which contains a suitable cleavage site, such as defined by the generic cleavage site X'UY', where X' and Y' represent any nucleotide (preferably wherein the cleavage site is GUC) as described previously. Most RNAs will contain one or more suitable cleavages sites.

The period of treatment would depend on the particular disease being treated and could be readily determined by a physician. Generally treatment would continue until the disease being treated was ameliorated.

Examples of human and animal disease which may be Herpes Simplex Virus infection (such as targeting cleavage of early gene 4 and 5), psoriasis, cervical preneoplasia, papilloma disease, HIV infection (such as targeting the HIV-1 gag transcript and HIV-1 5' ltr splice site), bacterial and prokaryotic infection, viral infection and neoplastic conditions associated with the production of aberrant RNAs such as occurs in chronic myeloid leukemia.

Further, the targets for the compound may be a viral gene including viral targets such as cytomegalovirus, hepatitis, herpes, HIV, EBV, papilloma virus, rhinovirus, influenza virus, varicella-zoster virus, parainfluenza virus, mumps virus, respiratory syncytial virus, adenovirus, measles virus, rubella virus, human parvovirus, poliovirus, rotavirus, echovirus, arbovirus, and human T cell leukemia-lymphoma virus.

An effective amount of a compound of the present invention would generally comprise from about 1 nM to about 1 mM concentration in a dosage form, such as a cream for topical application, a sterile injectable composition, or other composition for parenteral administration. In respect of topical formulations, it is generally preferred that between about 50 $\mu$M to about 500 $\mu$M endonuclease be employed. Compounds comprising nucleotide derivatives, which derivatives may involve chemically modified groups, such as phosphorothioate or methyl phosphonate derivatives may be active in nanomolar concentrations. Such concentrations may also be employed to avoid toxicity.

Therapeutic strategies involving treatment of disease employing compounds of this invention are generally the same as those involved with antisense approaches, such as described in the anti-sense bibliography of (Chrisley, 1991). Particularly, concentrations of compounds utilized, methods and modes of administration, and formulations involved may be the same as those employed for antisense applications.

An "effective amount" as used herein refers to that amount which provides a desired effect in a mammal having a given condition and administration regimen. Compositions comprising effective amounts together with suitable diluents, preservatives, solubilizers, emulsifiers, adjuvants and/or carriers useful for therapy. Such compositions are liquids or lyophilized or otherwise dried formulations and include diluents of various buffer content (e.g., Tris-HCL, acetate phosphate), pH and ionic strength, additives such as albumin or gelatin to prevent absorption to surfaces, detergents (e.g., Tween 20, Tween 80, Pluronic F68, bile acid salts), solubilizing agents (e.g., Thimerosal, benzyl alcohol), bulking substances or tonicity modifiers (e.g., lactose, mannitol), covalent attachment of polymers such as polyethylene glycol to the oligonucleotide, complexation with metal ions, or incorporation of the material into or onto particulate preparations of polymeric compounds such as polylactic acid, polyglycolic acid, polyvinyl pyrrolidone, etc. or into liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance of the oligonucleotide. Other ingredients optionally may be added such as antioxidants, e.g., ascorbic acid; low molecular weight (less than about ten residues) polypeptides, i.e., polyarginine or tripeptides; proteins, such as serum albumin, gelatin, or immunoglobulins; amino acids; such as glycine, glutamine acid, aspartic acid, or arginine; chelating agents such as EDTA; and sugar alcohols such as mannitol or sorbitol. Possible sustained release compositions include formulation of lipophilic depots (e.g., fatty acids, waxes, oils). Also comprehended by the invention are particulate compositions coated with polymers (e.g., polyoxamers or polyoxamines) and oligonucleotides coupled to antibodies directed against tissue-specific receptors, ligands or antigens or coupled to ligands of tissue-specific receptors. Further, specific nucleotide sequences may be added to target the oligonucleotides of this invention to the nucleus, cytoplasm or to specific types of cells. Other embodiments of the compositions of the invention incorporate particulate forms protective coatings, protease inhibitors or permeation enhancers for various routes of administration, including parenteral, pulmonary, nasal and oral.

Suitable topical formulations include gels, creams, solutions, emulsions, carbohydrate polymers, biodegradable matrices thereof; vapors, mists, aerosols, or other inhalants. The oligonucleotides may be encapsulated in a wafer, wax, film or solid carrier, including chewing gums. Permeation enhancers to aid in transport to movement across the epithelial layer are also known in the art and include, but are not limited to, dimethyl sulfoxide and glycols.

For in-vitro use, the compounds of this invention are generally reacted with a target RNA which contains one or more suitable cleavage sites. Optionally, the target RNA may be purified or substantially purified. The nucleotide sequences $(X)_N$ and $(X)_{N'}$ of the endonuclease of this invention are selected so as to specifically hybridize or form a double-stranded DNA duplex with a target RNA whereafter cleavage takes place. Accordingly, target RNA may be specifically cleaved in-vitro in the presence of other RNAs which themselves would not be cleaved.

The compounds may be utilized in a manner similar to restriction endonucleases, that is for the specific cleavage of RNA to facilitate RNA manipulation. All that is required for such manipulations is that the target RNA to be cleaved contains a uracil base and thus a suitable cleavage site.

The compounds of this invention may be utilized in diagnostic procedures, such as the mapping or fingerprinting of RNA. Specifically, the compounds of this invention would enable mapping of RNA and may be used to detect mutations in RNA sequence. Such procedures may be used in research and may also have forensic and other diagnostic applications.

RNA cleavage products in-vitro may be readily detected, for example, by visualization on acrylamide or agarose gels where the amounts of RNA cleaved are sufficiently large for direct visualization after separation and reaction with nucleotide visualization agents, such as ethidium bromide. Alternatively, where the target RNA cleaved is present in small amounts, such as in a sample containing many RNAs, cleavage products may, for example, be detected by using radiolabelled probes for sequence complementary to the target sequence, or amplification techniques such as PCR (Sambrook et al., Supra).

A target RNA for cleavage in-vitro may be derived from any source, and may be of animal, viral, bacterial, plant, synthetic, or other origin. As RNA is common to all known living organisms, this invention may be utilized to cleave any RNA species having a suitable cleavage site as mentioned previously.

This invention is illustrated in the Experimental Detail sections which follow. These sections are set forth to aid in an understanding of the invention but are not intended to, and should not be construed to, limit in any way the invention as set forth in the claims which follow thereafter.

Experimental Details

Experiment 1

Materials and Methods

Solid-Phase synthesis of Oligonucleotides. All oligonucleotides were synthesized on an Applied Biosystems 380 and/or 391 synthesizer by using 2-cyanoethylphosphoramidite chemistry. DNA monomers were from Applied Biosystems; RNA monomers, protected at the 2' position with a tert-butyldimethylsilyl group, were from Peninsula Laboratories or MilliGen (Bedford, Mass.). The 3'nucleotide in all molecules is a deoxyribonucleotide. All RNA-containing oligonucleotides, with 5'-trityl groups removed, were processed as follows. The oligonucleotide was cleaved from the column in $NH_4OH$/ethanol, 3:1, and heated overnight at 55° C. The solutions were evaporated to near dryness, coevaporated several times with $H_2O$/ethanol, 3:1, and then the amount of material was estimated by measuring UV absorbance. The 2'-group of the sugar was deprotected by treatment overnight with 1 M tetrabutylammonium fluoride in tetrahydrofuran (10 $\mu$l per $OD_{260}$ unit). The tetrabutylammonium ions were removed by passing the oligonucleotide solution twice through a Dowex 50X8-200 cation-exchange column in the $Na^+$ from; eluate volume was reduced by extraction with 2-butanol, and the oligonucleotide was precipitated with sodium acetate and ethanol. The oligonucleotide was then purified by electrophoresis on a 10–20% (depending on length) polyacrylamide gel containing 7 M urea. The band of interest was visualized by UV shadowing or ethidium bromide staining, excised, and soaked in several changes of water over 24 hr. The supernatant was removed from the gel slices, concentrated with 2-butanol, and extracted with phenol/chloroform and with ether. The oligonucleotide was then precipitated with sodium acetate and ethanol, washed with cold 80% ethanol, redissolved in 10 mM Tris HCl, pH 8.0/0.2 mM EDTA, quantified by UV spectroscopy, and frozen. The oligonucleotides were phosphorylated on their 5'-ends by using [$\gamma$-$^{32}$P] ATP and T4 polynucleotide kinase (Bresatec, Adelaide, Australia) under standard conditions, except that several units of ribonuclease inhibitor (RNasin, Promega) were added to the reaction mixture. The phosphorylation reaction was stopped with EDTA; the oligonucleotide solution was extracted with phenol/chloroform and ether and concentrated with 2-butanol. The 5'-end labeled oligonucleotide was precipitated twice, first from 2.5 M ammonium acetate and ethanol and secondly from 0.3 M sodium acetate and ethanol. The pellet was washed with cold 80% ethanol and then dissolved in 10 mM Tris.HCl, pH 8/0.2 mM EDTA to make a stock solution with nominal concentration of 1 $\mu$M. The exact concentration of the stock solution was determined in the following way. All supernatants from the two precipitation steps and the final ethanol were pooled, concentrated under vacuum, and loaded on denaturing polyacrylamide gel alongside a known, small fraction of the stock solution. After electrophoresis, gel slices containing the stock and the lost oligonucleotide were excised, and the amount of material they contained was quantified by Cerenkov counting. These data were used to determine the exact concentration of the 5'-end-labeled oligonucleotide solution.

Transcription of Oligonucleotides. One of the oligoribonucleotides used in this study ($MS_{4U,RNA}$) was transcribed from a DNA oligonucleotide containing a truncated T3 promoter. The DNA duplex was generated by extension with T7 DNA polymerase (Sequenase, United States Biochemical) after hybridizing two oligonucleotides with sequences as follows: T3 primer: 5' AAT TAA CCC TCA CTA (SEQ ID NO:19) and MS template: 5'-ACC TGC GGG TTT CAA AAT CAT CAG ATG AAG TGT CCG AAG ACA CTT CAT GAC CCG CAG GTA AAC CTT TAG TGA GGG TTA AAT (SEQ ID NO:20).

Another RNA molecule, the 173-nucleotide (nt) chloramphenicol acetyltransferase (CAT) substrate, was transcribed with T7 RNA polymerase from a Pvu II digest of pGEM3 containing the BamHI CAT fragment from pCM4 as described (Haseloff and Gerlach, 1988). Transcripts were made with the Stratagene transcription kits; a typical reaction in a 30-$\mu$l vol contained 5 pmol of template; 2 units of T3 RNA polymerase; 500 $\mu$M each of rATP, rGTP, and rCTP; 100 $\mu$M rUTP; 10 pmol of [$\alpha$-$^{32}$P]rUTP (17 $\mu$Ci; 1 Ci=37 GBq); 10 mM dithiothreitol; CAT RNA was stopped after 30 min, but $MS_{4U,RNA}$ was stopped after only 5 min to minimize self-cleavage of the transcribed molecule. The mixtures were extracted with phenol/chloroform; RNAs were precipitated with sodium acetate and ethanol, and the pellets were dissolved in sterile water. Concentration of the solution was determined by knowing the number of uridines in the sequence, the specific activity of the [$\alpha$-$^{32}$P]rUTP used, and the activity of an aliquot of the transcript solution.

Cleavage Reactions. Standard conditions for the cleavage reactions are as follows. Reactions were at 37° C. in a 30-$\mu$l vol of 10 mM $MgCl_2$/50 mM Tris-HCl, pH 8.0; the ribo/minizymes and substrate (labeled on the 5' end with $^{32}$P) were placed quickly on ice before mixing, adding $MgCl_2$, and incubating. At appropriate times, a 3-$\mu$l aliquot was removed from the reaction and added to 6 $\mu$l of quenching solution containing 80% formamide, 20 mM EDTA, and dye. The quenched samples were then analyzed by electrophoresis on 15% polyacrylamide gels containing 7 M urea as a denaturant. The substrate and product of cleavage were visualized by autoradiography, and gel slices corresponding to their positions were excised and quantified by Cerenkov counting. The ratio of [product] to ([substrate] plus [product]) was plotted versus time as shown. Rate constants were calculated by fitting, by a Newton-Raphson iterative procedure, data for percentage of product formed (%P) as a function of time (t) to an equation of the form %P=%$P_\infty$ is percentage of product at infinite time, C is the difference between percentage of product at t=$\infty$ and t=0, and k is the first-order rate constant. A listing of the program, which runs on MS-DOS computers, is available on request.

Nondenaturing Gels. The molecular species in a mixture that initially contained equimolar amounts (0.1 $\mu$M) of 5'-end-labeled substrate and ribozyme or minizyme and in which conditions for the cleavage reaction were as described above were analyzed under nondenaturing conditions by electrophoresis on 10% polyacrylamide gels kept at 4° C. After a 30-min reaction at 37° C., samples were mixed with an equal volume of 30% sucrose/0.1% dye and stored at −20° C. The polyacrylamide gels were preelectrophoresed for 2 hr next day after replacing the buffer with fresh solution (16, 17). Then samples were loaded and electrophoresed for 8 hr at constant voltage (400 V). In addition, the same samples were electrophoresed for 6 hr at 400 V on another 10% polyacrylamide gel, which was buffered by 90 mM Tris borate, pH 8/2 mM EDTA containing no $Mg^{2+}$. The components of several bands in the nondenaturing gels were determined by excising the bands, eluting the molecules in formamide, and separating them by electrophoresis on a denaturing, polyacrylamide gel; the 3'-product of cleavage of a 5'-end-labeled substrate is unobservable by this method.

Results and Discussion

The hammerhead ribozyme (Haseloff and Gerlach, 1988) is shown in FIG. 1 at top; its sequence (the two conserved regions are drawn in boxes) is at left, and a schematic drawing is at right. We call this ribozyme $R_{4U,RNA}$ and use it as a reference in assessing cleavage activities of other molecules. The RNA substrate for this ribozyme is also shown in FIG. 1 (top), where the cut site follows the cytidine residue marked by a downward arrow. The ribozyme and substrate together are designed to form two double helices each containing 10 base pairs (bp) on either side of the central cytidine. When the substrate is radioactively labeled at its 5' end, the cleavage reaction can be monitored easily by electrophoresing the reaction mixture on a denaturing polyacrylamide gel.

Figure 2:
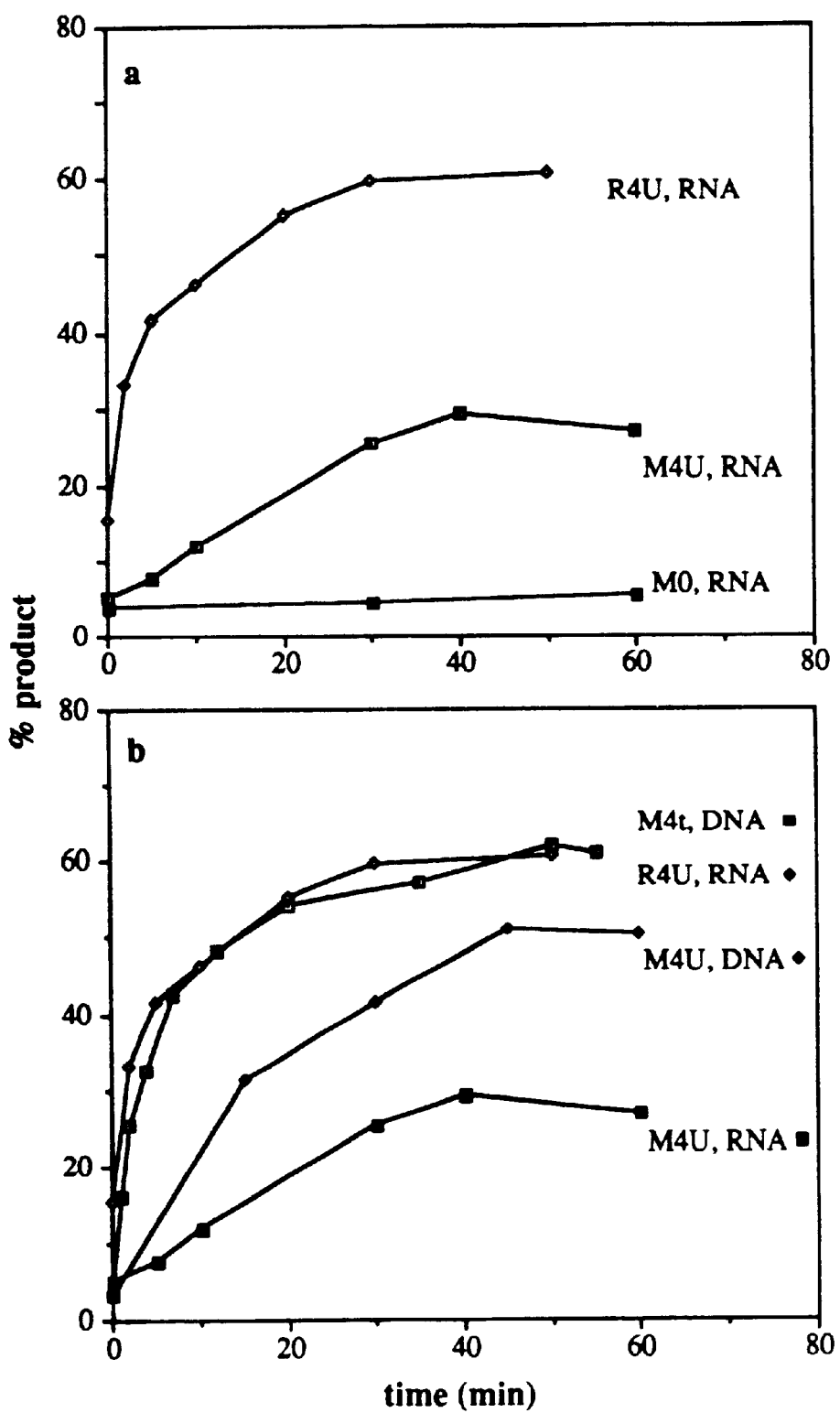
FIG. 2. Plots of percentage of product versus time for cutting of substrate by ribozyme and minizymes, labeled. Reactions were in 50 mM Tris-HCl, pH 8/10 MM $MgCl_2$ at 37° C.; substrate concentration was 0.1 $\mu$M, and ribozyme and minizyme concentrations were 0.6 $\mu$M in all reactions. (a) Effect of reducing size of an all-RNA ribozyme. (b) Effect of replacing RNA nucleotides by DNA in a minizyme of constant length. (Data in a for the ribozyme $R_{4U,RNA}$ are included in b for reference.)

To see how much a ribozyme could be reduced in size without complete loss of activity, we synthesized chemically, in small amounts, a series of RNA molecules that contained the conserved bases but omitted as many of the nonconserved bases as possible. A drastic reduction of the lower domain from 22 to 10 nt, shown in FIG. 1 as $M_{0,RNA}$, was unsuccessful in that it eliminated all RNA-cutting activity (FIG. 2a). But a less drastic reduction from 22 to 14 nt, shown in FIG. 1 as $M_{4U,RNA}$, preserved much cutting activity. The diminished ribozyme, $M_{4U,RNA}$, which lacks a helix II, is less active than the full-size ribozyme $R_{4U,RNA}$ (FIG. 2a, Table 1), but its measurable activity indicates that helix II (previously thought essential) is dispensable to the cleavage reaction. We defined a ribozyme that does not contain helix II as a "minizyme."

To see how many deoxyribonucleotides could be introduced into the minizyme ($M_{4U,RNA}$) without activity loss, we synthesized a series of molecules in which some or all of the nonconserved RNA nucleotides were replaced by DNA nucleotides. First, most of the ribonucleotides in the minizyme that contribute to forming double helices I and III were replaced with DNA (wavy lines in $M_{4U,DNA}$, FIG. 1). Unexpectedly, this minizyme with DNA arms cut the substrate to a greater extent than the all-RNA minizyme (FIG. 2b, Table 1). To continue the trend, all nucleotides connecting the two regions of conserved bases were replaced with DNA (wavy lines in $M_{4t,DNA}$, FIG. 1), and the RNA-cutting activity of this minizyme equaled that of the reference (FIG. 2b, table 1). Thus, we have made a diminutive ribozyme that contains just 12 RNA nt, with 4 DNA nt connecting the two regions of conserved RNA bases, and all DNA elsewhere in the helix-forming arms; and this small, DNA-rich molecule cleaves the substrate as well as the full-size, all-RNA ribozyme, at least for the particular substrate studied here. We have not attempted to replace any of the conserved ribonucleotides with DNA in the minizymes because such replacements in an all-RNA hammerhead ribozyme decrease its activity significantly (Perreault, et al., 1990, Perreault, et al., 1991). The increase in cleavage activity seen upon replacing ribonucleotides with deoxyribonucleotides in the minizyme probably arises from a slight alteration to the structure of the catalytic core of the minizyme-substrate complex; a different structure must be adopted by a ribozyme-substrate complex in which ribonucleotides are replaced by deoxyribonucleotides in the substrate, and for which an activity decrease is seen (Yang, et al., 1990).

To make the minizyme even smaller, the number of nucleotides in the helix-forming (hybridizing) arms may be reduced. We experimented with minizyme $M_{4t,DNA}$ and found that the number of base pairs in helices I and III can be reduced from 10 to 4, in both double helices, with maintenance of cleavage activity. Thus a minizyme can be at least as small as 22 nt.

Effect of Length and Sequence of the Connector. Within the small DNA-rich minizyme, the only nucleotides that can be varied now are those connecting the two regions of conserved RNA bases; all other nonconserved nucleotides are in the helix-forming arms and, hence, are determined by the base sequence of the target. Therefore, to find the optimal composition of the connector, new minizymes were designed based on the most active minizyme, $M_{4t,DNA}$. To find the optimal length, we compared the cleavage activities of four minizymes containing the DNA nucleotides 2T, 3T, 4T, 5T, or 6T in their connectors. Observed rate constants and %$P_\infty$ (Table 1) show that the 5T minizyme is marginally better than the 4T minizyme with shorter connectors. Presumably, a connector with <4T restricts the minizyme in adopting the active conformation of cleavage. To look at the effect of the 4-nt sequence, we compared cleavage activities of four minizymes containing the RNA nucleotides 4U, or the DNA nucleotides 4A, 4T, or 5'-TTCT in their connectors. observed rate constants and %$P_\infty$, (Table 1) indicate that, of this series, connectors of 4T and TTCT provide for the greatest activity. The connectors 4T and TTCT probably are sufficiently flexible to allow the conserved RNA nucleotides to adopt the active conformation for cleavage, whereas the connectors 4A and 4U are more rigid in structure, with possible stacking of adenine bases in 4A and interactions involving 2'-hydroxyl groups in 4U (Saenger, 1984). Goodchild and Kohli (Goodchild and Kohli, 1991) also have reduced the number of nucleotides joining the two stretches of conserved RNA bases in a hammerhead ribozyme, although they kept bases that potentially could form Watson-Crick pairs (and, potentially, a ribozyme dimer). One of their all-RNA molecules, which has the sequence 5'-GGCC in the equivalent of our connector, cleaves its substrate very slowly. A second molecule, which has 5'-GGCGCC in the connector, cleaves the same substrate with higher initial rates. Because the structure of these two connectors would be relatively rigid, due to stacking of guanine bases (McCall et al. 1985) and the possible formation of a GC base pair, a connector >4 nt is probably necessary to allow their enzyme to adopt the active conformation. These initial results suggest that further improvement of the cleavage activity of minizymes may be possible.

TABLE 1

Kinetic data for cleavage by various minizymes

| Ribozyme/minizyme | Rate constant, $min^{-1}$ | % $P_\infty$ |
| --- | --- | --- |
| $R_{4U,RNA}$ | 0.15 | 59 |
| $M_{4U,RNA}$ | 0.05 | 31 |
| $M_{4U,DNA}$ (4U) | 0.05 | 54 |
| $M_{4t,DNA}$ (4T) | 0.16 (0.03) | 62(5) |
| $M_{2t,DNA}$ (2T) | <0.001 | — |
| $M_{3t,DNA}$ (3T) | 0.014 | 65 |
| $M_{5t,DNA}$ (5T) | 0.23 | 71 |
| $M_{6t,DNA}$ (6T) | 0.23 | 62 |
| $M_{4a,DNA}$ (4A) | 0.02 | 64 |

TABLE 1-continued

Kinetic data for cleavage by various minizymes

| Ribozyme/minizyme | Rate constant, min$^{-1}$ | % P$_\infty$ |
| --- | --- | --- |
| M$_{ttct,DNA}$ (TTCT) | 0.21 | 76 |
| M$_{4t,Krüp-DNA}$ + Krüppel substrate | 0.23 | 76 |
| M$_{4t,CAT-DNA}$ + short CAT substrate | 0.03 | 70 |
| M$_{4t,CAT-DNA}$ + long CAT substrate | 0.02 | 94 |

Reactions were in 50 mM Tris-HCl, pH 8/10 mM MgCl$_2$ at 37° C.; substrate concentration was 0.1 μM and ribozyme and minizyme concentrations were 0.6 μM. Except where indicated otherwise, the substrate is that shown at top of FIG. 1. Minizyme M$_{4t,DNA}$ was synthesized several times, and its kinetics of cleavage was determined independently on four separate occasions; SDs of the mean rate constant and mean percentage of product at infinite time (%P$_\infty$) are in parentheses.

Figure 3:
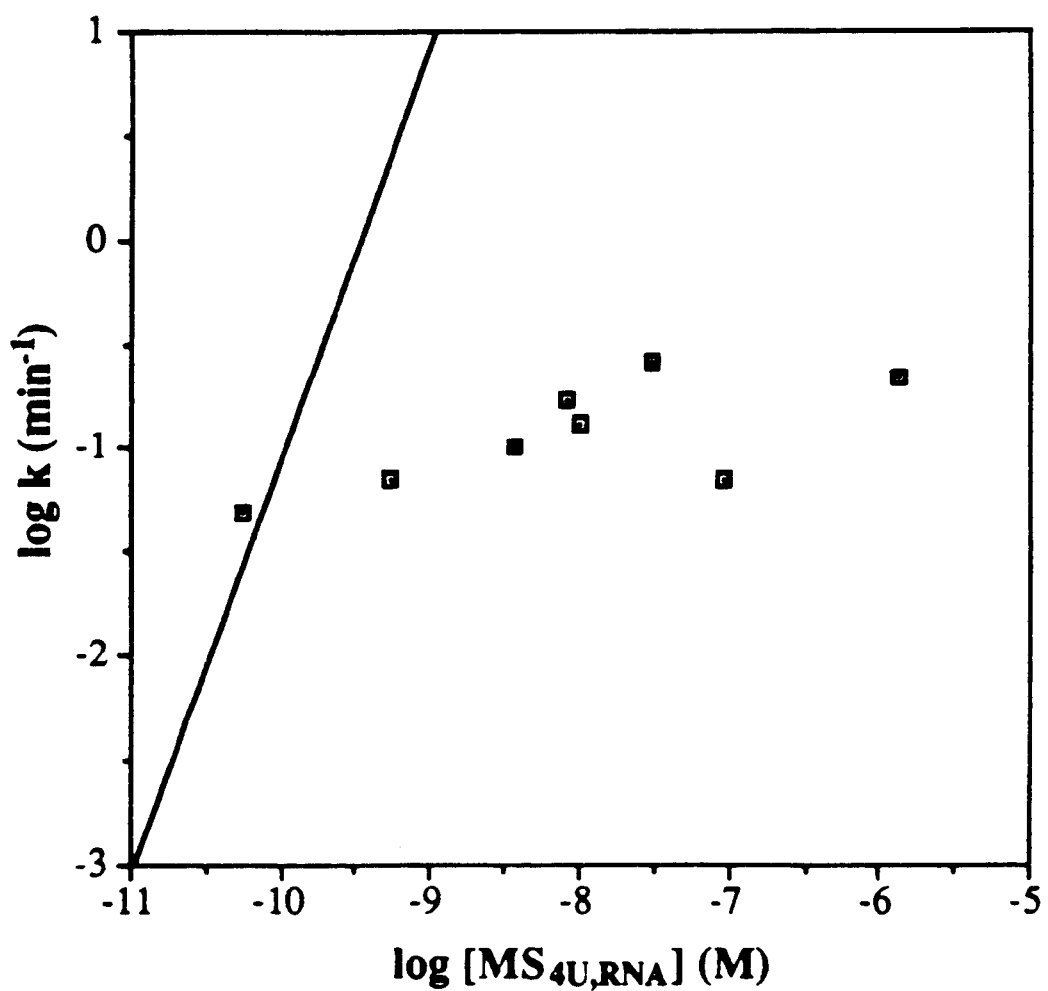
FIG. 3. Observed rate constants (□) for the self-cleavage of the unimolecular minizyme-substrate $MS_{4U,RNA}$ at various concentrations. Reactions were at 37° C. in 50 mM Tris-HCl, pH 8/10 mM $MgCl_2$. Solid line represents the expected variation of rate constant with concentration (k α concentration$^2$), were the reaction bimolecular and dimer-formation rate limiting.

Minizymes are Active as Monomers. We considered whether some form of helix II might arise from the association of bases in the connectors of two minizyme molecules and whether such a minizyme dimer was the active species. A precedent exists for this: Forster et al. (Forster, et al., 1988) have proposed that self-cleavage of RNA occurs for avocado sunblotch viroid and in cleavage of RNA from the newt by the combination of two different hammerhead domains to form active dimers. However, results from the following three experiments indicate that the minizyme acts as a monomer. (i) For M$_{4t,DNA}$, the putative helix II would be formed by T-T base pairs, which are relatively unstable. A more stable helix II, consisting of T-A base pairs, might be formed by mixing M$_{4t,DNA}$ with M$_{4a,DNA}$; and, were dimerization required for cleavage, the mixed minizyme-dimer should be more active than the dimers formed by either component alone. Cleavage of substrate (0.4 μM) by M$_{4t,DNA}$ (0.4 μM), by M$_{4a,DNA}$ (0.4 μM), and by M$_{4t,DNA}$ mixed with M$_{4a,DNA}$ (0.2 μM each) was followed under standard conditions. The observed rate constants for the reactions (0.14 min$^{-1}$ for M$_{4t,DNA}$, 0.02 min$^{-1}$ for M$_{4a,DNA}$, and 0.04 min$^{-1}$ for M$_{4t,DNA}$ mixed with M$_{4a,DNA}$) indicate no synergy between the two minizymes in cleaving substrate. (ii) The transcribed oligonucleotide MS$_{4U,RNA}$, which has a minizyme and attached substrate (see FIG. 1, bottom), shows little change in the rate constant for cleavage (≈0.1 min$^{-1}$) over a concentration range varying 25,000-fold from 1.3 μM to 55 pM (data points in FIG. 3). Were the concentration of MS$_{4U,RNA}$ in the cleavage reactions significantly less than the association constant for the putative dimerization, the rate of cleavage by the dimer would be expected to depend on the square of the concentration (solid line in FIG. 3); the data do not following this relation ship. (iii) Complexes of a ribozyme and two different minizymes with various cleavable and noncleavable substrates were analyzed by electrophoresis on a 10% polyacrylamide gel under non-denaturing conditions (FIG. 1). A single complex is formed between the minizyme M$_{4t,DNA}$ and its noncleavable substrate, as revealed by the strong band in lane 11, set B, of FIG. 4. This complex moves in the gel as a species of ≈31 bp, slightly ahead of the 34-bp DNA marker i lane 1. [This estimate of size in bp of a DNA-RNA complex probably represent an upper limit because mobilities of double-stranded RNA molecules and probably, of double-stranded RNA-DNA molecules in nondenaturing gels are 10–20% lower than the corresponding mobilities of duplex DNA (Gast et al., 1991)]. A complex formed by one minizyme (34 nt) and one substrate molecule (21 nt) would contain 55 nt or formally, 27.5 bp. Therefore, in this complex, there is just one minizyme molecule. The adjacent lane 10 contains the same minizyme M$_{4t,DNA}$ with its cleavable substrate. The strong band at ≈31 bp in lane 10 was shown to consist of minizyme, uncleaved bp in lane 10 was shown to consist of minizyme, uncleaved substrate, and the 5'-product of cleavage. Other bands lower down lane 10 were shown to contain the minizyme plus the 5'-product, the minizyme plus (presumably) the 3'-product and, at the gel bottom, the 5'-product alone. There are no species of molecular mass >≈31 bp in either lane 10 or 11. Similar results were obtained for a different, 21-nt, cleavable substrate and it respective, 34-nt minizyme (compare lane 6, set A, with lane 10 set B, of FIG. 4), indicating that these observations probably are general for minizymes. Therefore, all available evidence is consistent with minizymes acting as monomers.

Figure 4:
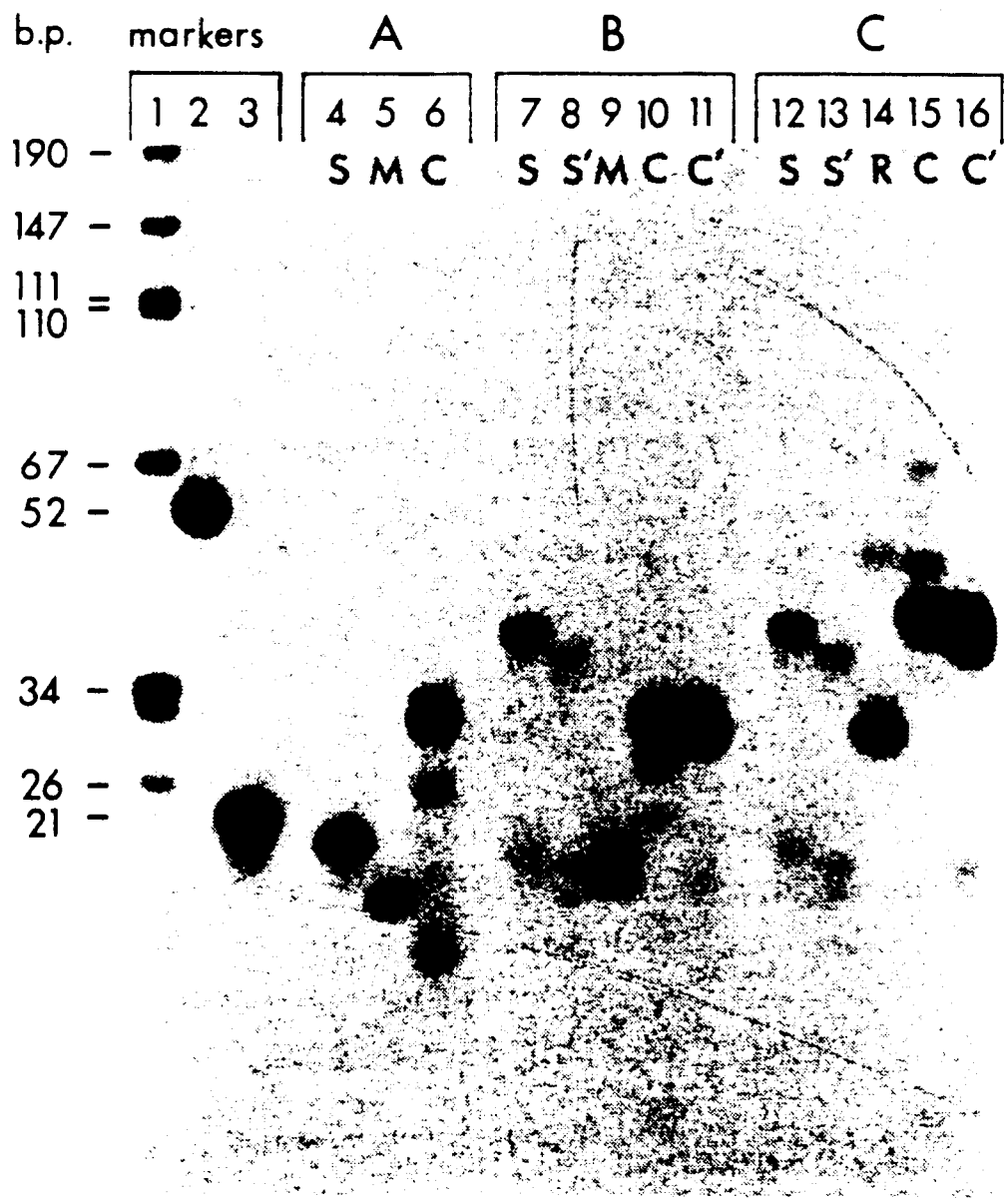
FIG. 4. Mobilities of various substrates, minizymes, and ribozymes, and their complexes and products of cleavage in a non-denaturing, 10% polyacrylamide gel at 4° C. The electrophoresis buffer was 50 mM Tris borate, pH 8/10 mM $MgCl_2$. Species in each of lanes 4–16 represent the reaction products for 30 min at 37° C. under standard conditions. S, substrate only in reaction: S' noncleavable substrate; M, minizyme; R, ribozyme; C, equimolar mix of substrate and minizyme (or ribozyme); and C', equimolar mix of non-cleavable substrate and minizyme (or ribozyme). The molecules in set A (lanes 4–6) are an all-RNA, 21-base synthetic substrate of sequence 5'-AUUUGCGAGU CCACACUG-GAG (SEQ ID NO:8)(from the Krüppel gene of Drosophila malanogaster) and its cognate, 34-base minizyme based on $M_{4t,DNA}$; those in set B (lanes 7–11) are the all-RNA, 21-base substrate described in FIG. 1, a noncleavable substrate of identical base sequence in which the central ribocytidine has been replaced by a deoxyribocytidine, and the minizyme M$_{4t,DNA}$; those in set C (lanes 12–16) are the same cleavage and noncleavable substrates of set B and ribozyme R$_{4U,RNA}$. Size markers are labeled in base pairs. Lanes: 1, DNA double helices formed by a Hpa II restriction digest of pUC19; 2, 52-bp DNA double-helix; and 3, 21-bp double helix consisting of an all-RNA strand identical to the molecule in lane 4 and an all-DNA strand of complementary sequence. To clearly see the bands of interest, the gel above the 190-bp mark is not shown; there were no bands above this mark in lanes 2–16.

Other pertinent information can be drawn from FIG. 4 (i) A single complex, which moves in the gel as an ≈42-bp species, is formed by the ribozyme R$_{4U,RNA}$ (42 nt) and its noncleavable substrate (21 nt), as shown by the strong band in lane 16, set C, of FIG. 4, A 1:1 complex of these molecules would contain 63 nt or, formally, 31.5 bp. The same ≈42 bp species is present in lane 15 of FIG. 4; it was shown to consist of ribozyme, uncleaved substrate, and the 5'product of cleavage, analogous to the minizyme-substrate complexes in lanes 6 and 10. In addition, lane 15 reveals that some higher-polymeric species are present in very small amounts in the reaction mixture. All these species, which appear reproducible, were shown to contain ribozyme, uncleaved substrate, and product of cleavage. These higher molecular-mass species depend on Mg$^{2+}$ for stability because they are absent in 10% polyacrylamide gels buffered by 90 mM Tris borate/2 mM EDTA. Therefore, from the experiments on gel mobility, we conclude that this full-size ribozyme acts predominantly as a monomer in forming a complex with is substrate. (ii) The presence of uncleaved substrate complexed with minizyme and ribozyme in the reaction mixtures suggests that a proportion of the complexes might not be in the active conformation for cleavage; this would account for the observed extents of cleavage being <100% in FIG. 2 and Table 1. (iii) The minizyme-substrate complex migrates in the gel as an ≈31 bp species, which is only slightly slower than would be expected were it a regular double helix of 27.5 bp. Because the mobility of a molecule in a gel is determined by its convex volume (the volume occupied by an imaginary, convex hull enveloping the molecule) (Calladine, et al., 1991), this suggests that helices I and III in the complex are approximately parallel and that the conserved nucleotides protrude very little beyond the surface of these helices.

Cleavage of Other Substrates. To see whether minizymes were active generally against other RNA molecules, we synthesized two more minizymes based on M$_{4t,DNA}$ but with appropriate changes to the sequence of the flanking arms. The new substrates were synthetic oligonucleotides of 21 bases; one of these is the Krüppel substrate described in set A of FIG. 4, and the other, of sequence 5'-GCAUUUCAGUCAGUUGCUCAA, (SEQ ID NO:21) is part of the gene for CAT. These short substrates were cleaved by their respective minizymes at the expected sites, as judged by counting bands on a denaturing polyacrylamide gel that had the products of the cleavage reactions directly beside the products of alkaline hydrolysis of the respective substrates. To test the activity of minizymes against a longer RNA substrate, we made a 173-nt CAT transcript (Haseloff and Gerlach, 1988) containing the sequence of the shorter substrate, in which the expected cleavage site was 139 nt from the 5' end. The minizyme cleaved the transcript at the expected site, as judged by sizes of the cleavage products. Rate constants and %$P_\infty$ measured for these reactions under standard conditions are given in Table 1.

A further series of growth hormone RNA targeted endonucleases were synthesized based on the $M_{4t,DNA}$ construct and having different types of nucleotides connectors. For example, MttPDt, DNA where PD refers to 1,3-propanediol which was used in place of a nucleotide.

Kruppel RNA

The endonuclease M4t.DNA, Kr1079 (comprising 34 nucleotides and having flanking sequences of DNA designed to hybridize to the Kruppel target RNA) was tested against a short synthetic RNA substrate of 21 nucleotides and a RNA substrate of approximately 1.9 Kb, both containing the same cleavage site.

The Kr RNA transcript was prepared by inserting cDNA encoding the Kr transcript into a plasmid containing the T7RNA polymerase promoter. The Kr transcript was then transcribed with T7-polymerase.

The synthetic 21 mer was chemically synthesized and contained the same cleavage site as the longer RNA transcript. The 21 mer comprised the following sequence:

A U U U G C G A G U C* C A C A C U G G A G where C* is a ribonucleotide.

In-vivo testing of activity of an anti-Kruppel endonuclease could be accomplished by microinjection of Drosophila embryos prior to the stage of syncytial blastoderm, in order to inactivate the 2.3 Kb RNA Kruppel transcript. Embryos (cuticlised embryos) can be assayed for abberant segmental pattern one to two days after egg laying.

Platelet Derived Growth Factor (PDGF)

The endonuclease Mttct,DNA, PDGF (a 30 mer, having flanking DNA sequences designed to hybridize to the PDGF target RNA) was reacted with a 666 base RNA transcript corresponding to exons 2 and 6 of the PDGF A gene from human. A 666 base pair RNA transcript was transcribed in-vitro from a PDGF gene fragment using T3 polymerase.

In summary, cleavage activity of a ribozyme of the Haseloff-Gerlach type can be maintained despite size reduction and replacement of many RNA nucleotides by DNA. One of the three conserved double helices, helix II, is dispensable to formation of the active structure. The minimized ribozyme, or minizyme, is active as a monomer. We think that these minizymes will be useful in future structural and functional studies of catalytic RNA. They should also prove useful in gene-control studies in living cells (Cotten and Birnstiel, 1989; Cameron and Jennings, 1989; Sarver, et al., 1989; Saxena and Ackerman, 1990), where the DNA component should make them more resistant to RNase.

Experiment 2

Materials and Methods

All oligonucleotides were prepared by solid-phase methods using 2-silyl-protected phosphoramidites (Milligen) for RNA (benzoyl-protected A, G and C) and phosphoramidite monomers for DNA (Applied Biosystems). The oligonucleotides were deprotected as described above (see McCall, et al., 1992), and purified by electrophoresis on 10–20% polyacrylamide gels (depending on the length of the oligonucleotide) containing 7M urea, also as described (McCall et al., 1992). The purity of each oligonucleotide was checked by labelling its 5'-terminus with $^{32}P$ phosphate using T4 polynucleotide kinase molecules by autoradiography. The concentrations of the purified oligonucleotides were determined by UV spectroscopy using the following molar extinction coefficients for the various nucleotides at 260 nm; A, 15.4 ×$10^3$; G, 11.7×$10^3$; C, 7.3×$10^3$; T, 8.8×$10_3$; U, 10.0×$10^3$. All oligonucleotides were stored in either water or 10 mM Tris.Cl, pH 8.0, 0.2 mM EDTA at −20° C.

Enzyme kinetic experiments were conducted in 50 mM Tris.Cl, pH 8.0, 10 mM $MgCl_2$, at 30° C. The concentration of the all-RNA substrate (S13, FIG. 5) ranged from 10 to 200 nM, and the concentration of both ribozyme 2 (FIG. 5) was 0.77 nM. Initial-rate measurements were made up to 15% cleavage of the substrate. Neither ribozyme nor substrate were heat-treated before initiating the reaction by adding the substrate. Reactions in 20–40 23 μl volumes were performed in 96-well polypropylene tissue-culture trays, as these were found to absorb less ribozyme or substrate than either siliconized or autoclaved Eppendorf tubes. Samples of 2–3 μL were removed at given times and quenched with 2 volumes of 80% formamide containing 20 mM EDTA and dye. Samples were analyzed by electrophoresis on 15% denaturing, polyacrylamide gels, followed by autoradiography and excision of the bands corresponding to the substrate and 5'cleavage product. The amounts of radioactivity in the bands were quantitated by Cerenkov counting. Enzyme kinetic data were analyzed by Eadie-Hofstee plots to yield $K_m$ and $V_{max}$. It was found that $K_m$ and $V_{max}$ from individual experiments varied by up to a factor of 2, and therefore the initial rates at each concentration, from at least 4 independent experiments, were averaged and plotted in the form of rate versus rate/[substrate] to yield the kinetic parameters in Table 2.

Experiments with ribozyme in excess of the substrate S13 were also conducted in 50 mM Tris.Cl, 10 mM $MgCl_2$, at 30° C.: the concentrations of the ribozymes were 1.5 μM and the substrate was 500 nM. The ribozyme and substrate were heated together to 75° C. for 3 minutes, then allowed to cool to 30° C. for 1–2 minutes before initiating the reaction by adding the magnesium-containing buffer. The kinetic parameters were obtained by fitting the data for percentage of product formed versus time to the equation:

$$P_t = P_\infty - (\exp(-kt)P_v)$$

where $P_t$ is the percentage of product at any given tine, $P_{28}$ is the percentage of product at t=∞, k is the first-order rate constant for the reaction, t is the time, and $P_\infty$ is the difference between the percentage of product at t=∞ and t=0. This is a conventional first-order kinetic equation from which k, $P_{28}$ and $P_v$ are determined by least-squares fitting of the data. The quoted rate constants and $P_\infty$ values in Table II are the mean (± SD) for at least 2 independent experiments. In the time-scale of these experiments, the reactions do not proceed to 100%.

Kinetics of cleavage of the DNA substrate containing a ribocytodine at the cleavage site (S21D, FIG. 1) were conducted under conditions identical to those described above for the experiments with S13, except that the concentrations of the ribozymes were 1.5 μM and the substrate was 200 mM.

Stability of the ribozymes in serum was determined by incubating the ribozymes, labelled at the 5' end with $^{32}P$ phosphate, in various concentrations (to 0.01%) of fetal calf serum (Cytosystems). Samples were removed at various times EDTA and dye, and then quickly frozen on dry ice. The solutions were thawed immediately prior to loading on to a 10% denaturing (7 M urea) polyacrylamide gel for analysis. Percentage ribozyme remaining at these times was determined by excising gel fragments corresponding to the position of the full-length ribozyme and quantitating by Cerenkov counting.

Results and Discussion
Cleavage of the RNA substrate

Figure 5:
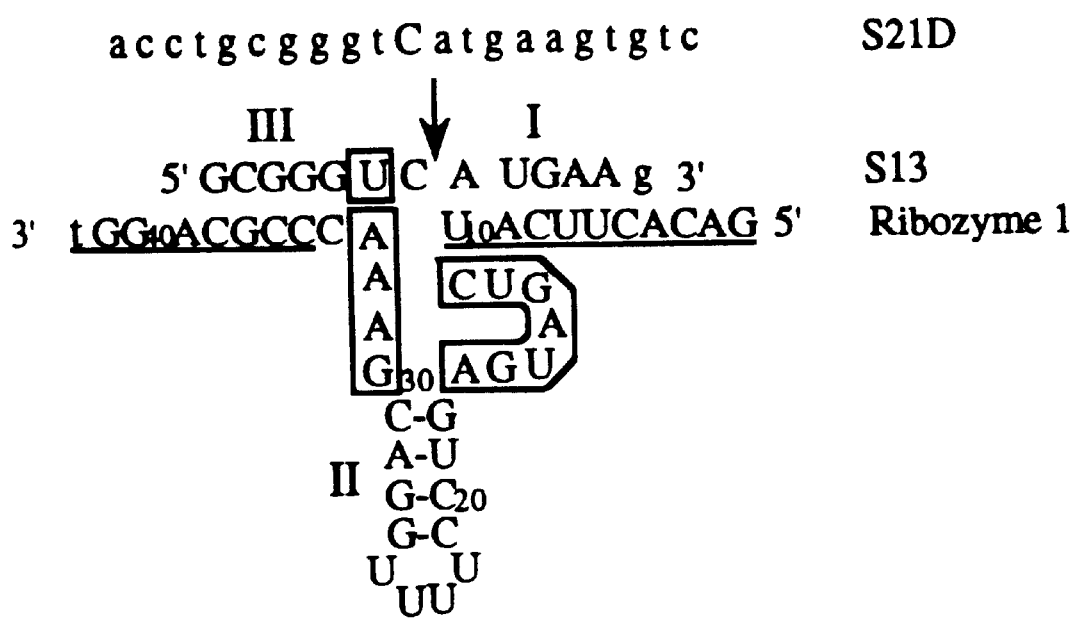
FIG. 5. Sequences of the ribozymes and substrates used in this study. Lower case letters are deoxyribonucleotides, upper case letters are ribonucleotides, and boxed letters are conserved nucleotides. S21D (SEQ ID NO:9), S13(SEQ ID NO: 10), Ribozyme 1(SEQ ID NO:11). Ribozyme 2(SEQ ID NO:12) has the same sequence as ribozyme 1, except that the underlined letters are all deoxyribonucleotides in ribozyme 1 with U$_6$, U$_7$ and U$_{10}$ being replaced by T. Roman numerals label double helices. All oligonucleotides used in this study have a 3'-deoxyribonucleotide.

Ribozyme 1 is an all-RNA hammerhead ribozyme with the sequence shown in FIG. 5. Ribozyme 2 is an analogous ribozyme in which the non-conserved nucleotides in the hybridizing arms, underlined in FIG. 5, are DNA, and all other nucleotides are RNA. As described in Experiment 1, we have observed that when helix II was removed from ribozyme 1 and replace by a 4-nucleotide linker, a very large proportion of the resultant loss in activity could be regained by placing DNA in the hybridizing arms of the minimized ribozyme (McCall et al., 1992). Therefore, we synthesized ribozyme 2 in order to see if an increase in activity also could be achieved by placing DNA in the hybridizing arms of a normal hammerhead ribozyme.

The cleavage reactions were analyzed according to Scheme 1, using Michaelis-Menton equations. In the scheme, S is substrate, R is ribozyme, and P1 and P2 are the cleavage products. The scheme is a simplification of the real situation since (i) it does not allow for alternate conformations of any of the participants and (ii) the dissociation of the products of the reaction is undoubtedly a multistep process. However, it is acceptable to approximate the product dissociation to a single step since one of the products, by virtue of its G/C content, is expected to dissociate from the ribozyme much more slowly than the other; and the question of alternate conformations will be addressed as it arises.

Scheme 1

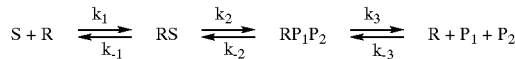

Table 2 vide infra shows the values of the catalytic constant, $K_{cat}$ ($k_{cat}=V_{max}/[\text{ribozyme}]$) and the Michaelis constant, $K_m$, for ribozymes 1 and 2 in reactions, with an RNA substrate of 13 nucleotides at 30° C., $k_{cat}$ for ribozyme 2, 8, 9 min$^{-1}$, is 20-fold higher than for ribozyme 1. The $k_m$'s for the two ribozymes differ slightly, with ribozyme 1 having the lower value, 38 nM. The ratio $k_{cat}/k_m$, which is often used as a measure of the relative efficiency of enzymatic activity, is 10 min$^{-1}$ $\mu M^{-1}$ for ribozyme 1 and 150 min$^{-1}$ $\mu M^{-1}$ for ribozyme 2.

The catalytic constant of 8.9 min for the DNA-armed ribozyme in reaction with an RNA substrate is, to our knowledge, the highest yet observed for any ribozyme with $Mg^{2+}$ as the activating ion. A value of $k_{cat}$ of 41 min$^{-1}$ has been reported by Olsen et al. (Olsen, et al., 1991) for a hammerhead ribozyme activated with $Mg^{2+}$, but the same ribozyme activated by $Mg^{2+}$ has a $k_{cat}$ of only 2.1 min$^{-1}$ at 25° C.

Experiments to measure the first-order rate constant for cleavage of the substrate (data in Table 3) were conducted under conditions where all the available substrate was expected to be bound in ribozyme. The substrate concentration of 500 mM was about 10-fold greater than the $k_m$ for the reactions, and the ribozyme was present in 3-fold excess over the substrate. In addition, the ribozyme and substrate were heated together in the absence of $Mg^{2+}$, and then cooled together to the reaction temperature, thus assisting the formation of ribozyme-substrate complexes. The reaction was initiated by the addition of the $Mg^{2+}$ containing buffer. Under these conditions the rate-limiting step is almost certainly the cleavage step, since the ribozyme-substrate complex should be fully formed, the addition of $Mg^{2+}$ is expected to be rapid, and the product dissociation is irrelevant in these conditions. Hence, the observed rate constant is equal to $k_2$ in scheme 1 and should equal $k_{cat}$ for the turnover reaction, if in the turnover reactions the cleavage step is rate-determining.

The rate constant, $k_2$, observed for the cleavage of S13 by ribozyme 1, 5 min$^{-1}$, is slightly less than the kcat of 8.9 min$^{-1}$ observed for the reaction under similar conditions. This difference is not significant, given the following experimental limitations. In the turnover experiments to determine $k_{cat}$, absolute concentrations of both the ribozyme and the substrate are important in determining the kinetic parameters. Additionally, the trace amount of ribozyme used make the results of the experiments subject to error due to absorption of the ribozyme on to the surface of the reaction vessels. In the experiments to independently determine $k_2$, the kinetic data are independent of absolute concentration of both ribozyme and substrate; however, in this case, the rates of the reactions ($t_{1/2} \approx 8$ seconds for ribozyme 2) make it difficult to determine the rate constants accurately. Therefore, it is reasonable to assume that the limiting step in the turnover reaction for ribozyme 2 is the cleavage step.

On the other hand, the observed rate constant of 1.6 min$^{-1}$ for the cleavage of S13 by ribozyme 1 is 4-fold greater than the $k_{cat}$ of 0.4 min. for the turnover reaction. This discrepancy is too large to be accounted for by experimental error, and it suggest that for ribozyme 1 the cleavage step is not rate-determining. In the cleavage of S13 under conditions where the ribozymes were in excess, less than 100% of the substrate was cleaved: this is due to the formation of inactive ribozyme-substrate complexes (McCall, et al., 1992). Heat-pulsing the reaction mixture of 75° C. for 3 minutes, followed by incubation of 30° C., allows the reaction to proceed further (data not shown). This observation suggests that the measured values of kcat underestimate the activity of the ribozymes in the active complex. The error is likely to be more significant for ribozyme 1 than for ribozyme 2, since in the experiments with ribozyme in excess only 50% of S13 was cleaved by ribozyme 1 but 62% was cleaved by ribozyme 2 (Table 3). Assuming this to be the case for the turnover experiments as well, then the measured kcat of 0.4 min$^{-1}$ for ribozyme 1 (the average for both the inactive and active complexes) should be increased to ≈0.8 min$^{-1}$ for the active complex alone. This value is closer to the independently-measured $k_2$, but still differs from it by a factor of 2, and so alternatives to the cleavage reaction being rate-determining must be considered. If the dissociation of one or both products from the ribozyme were rate limiting, a burst of product would be observed at the beginning of the reaction; this was not observed for either ribozyme. If the rate of formation of complex were rate limiting for ribozyme 1, as may be the case, then the likelihood is that ribozyme 1, when uncomplexed, adopts a conformation which is not readily able to bind the substrate. This conformation must be stabilized, relative to ribozyme 2, by the all-RNA hybridizing arms. The rate-limiting step then becomes the rate of unfolding of this ribozyme into a form capable of binding the substrate, and this unfolding rate may be exacerbated by longer-than-necessary hybridizing arms. Further experiments are necessary to unambiguously determine the rate-limiting step for ribozyme 1.

The $k_m$'s for DNA and RNA substrates with all-RNA ribozymes have been found to differ by 6- to 16-fold in one study (Yang, et al., 1990) and were estimated to be 100-fold greater for the DNA substrate in another (Dahm and Uhlenbeck, 1990). In contrast, in our study where the DNA is introduced into the ribozyme, the $K_m$ for ribozyme 2 with the RNA substrate is only 1.5-fold greater than found for ribozyme 1. In Michaelis kinetics, $K_m=(k_{-1}+k_2)/k_1$, $k_2$ has been measured for both ribozymes and is 3-fold greater for ribozyme 2, and $k_{-1}$ is expected to be greater for ribozyme 2 than ribozyme 1 because of the expected, relatively weaker binding in DNA/RNA duplexes. It follows therefore that $k_1$ for ribozyme 2 must also be greater than for ribozyme 1 in order for the difference in Km's to be as small as observed. This reduction in apparent $k_1$ for ribozyme 1 relative to ribozyme 2 supports the above speculation about an alternate conformation for ribozyme 1 which limits the rate of association with substrate.

TABLE 2

Results of turnover experiments with substrate S13

| Ribozyme | $k_{cat}$ (min$^{-1}$) | $K_m$ (nM) | $k_{cat}/K_m$ (min$^{-1}$ $\mu$M$^{-1}$) |
|---|---|---|---|
| ribozyme 1 | 0.40 | 38 | 10 |
| ribozyme 2 | 8.9 | 59 | 150 |

Conditions: 30° C., pH 8.0, 10 mM MgCl$_2$

TABLE 3

Rate constants and % product formed at infinite time (calculated) for the cleavage of substrate S13 (all-RNA) and substrate S21D (DNA with ribo C at cleavage site) by ribozymes 1 and 2 when in excess over substrate

| Ribozyme | $k_2$ (min$^{-1}$) | % P$_\infty$ |
|---|---|---|
| ribozyme 1 + S13 | 1.6 ± 0.6 | 49 ± 3 |
| ribozyme 2 + S13 | 5.0 ± 1.0 | 61.5 ± 2 |
| ribozyme 1 + S21D | 0.044 ± 0.004 | 50 ± 1 |
| ribozyme 2 + S21D | 0.12 ± 0.01 | 70 ± 1 |

Conditions as for Table 2.

Cleavage of the DNA Substrate

Figure 6:
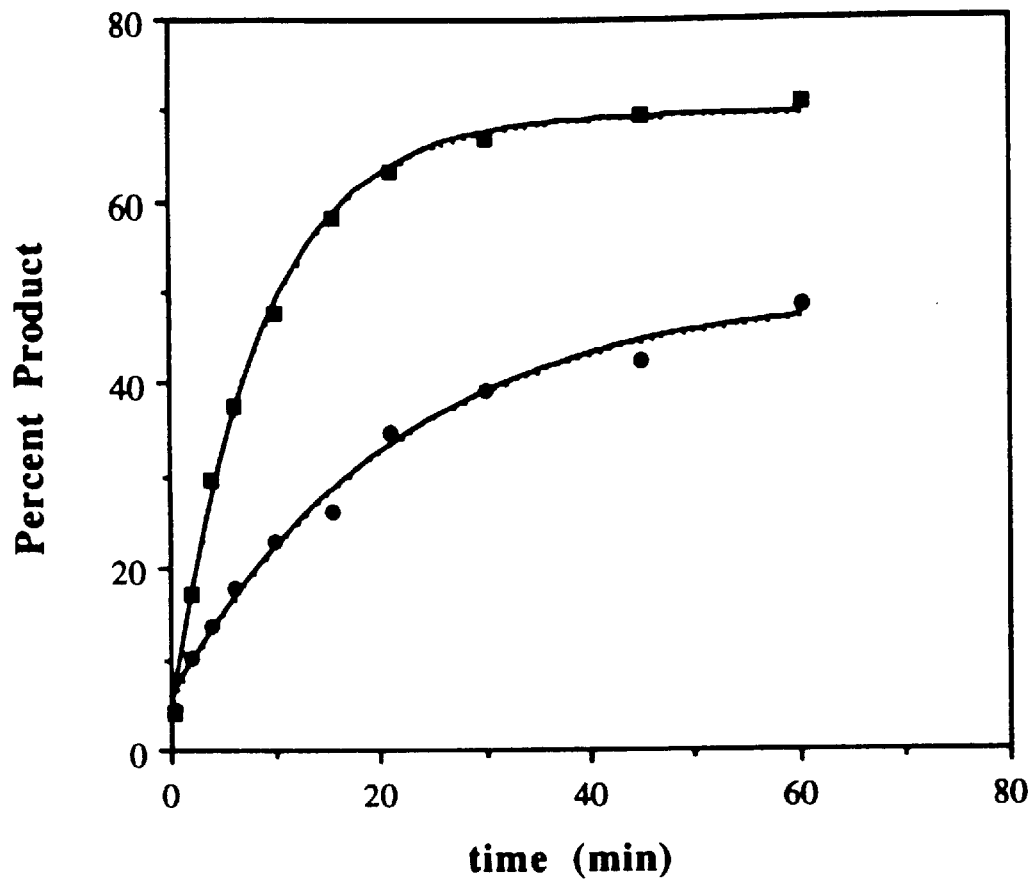
FIG. 6. Percent product versus time for reaction of ribozyme 1 ● and ribozyme 2■, with substrate S21D at 30° C., 50 mM Tris.Cl, pH 8.0 and 10 mM MgCl$_2$; concentration of ribozyme was 1.5 μM and substrate, 200 mM. solid lines are lines of best fit to the data, using the first-order kinetic equation given in the Methods section.

The cleavage of the DNA substrate, S21D, by the two ribozymes was performed under conditions where the ribozyme-substrate complex was expected to be fully formed prior to addition of Mg$^{2+}$ to initiate the reaction. The substrate in this case was chosen to be 21 nucleotides to compensate for the expected weaker binding of ribozymes to a DNA substrate compared with an RNA substrate. Use of the longer substrate should not result in serious discrepancies in comparing data, since the rate of cleavage of the complex is not expected to depend strongly on the length of the substrate. FIG. 6 shows an example of the data used to determine the rate constants. The data fit the first-order model well. The observed rate constants for cleavage of the DNA substrate are given in the lower half of Table 3. $k_2$ for ribozyme 2 (0.12 min$^{-1}$) is 3 times greater than for ribozyme 1, the same ratio as observed for cleavage of the all-RNA substrate by these ribozymes. The absolute values for rates of cleavage of the DNA substrate are approximately 40-fold less than observed of the DNA substrate are approximately 40-fold less than observed in earlier studies (Yang, et al., 1990; Dahm and Uhlenbeck, 1990). Why should DNA in the substrate decrease the rate of cleavage, but DNA in the arms of the ribozyme increase the rate? It is known that the 2'-hydroxyl of the uridine immediately 5'to the cleavage site on the substrate is involved in binding the Mg$^{2+}$ on (Yang, et al., 1990). However, even if both that important uracil and the cytosine at the cleavage site are ribonucleotides, and the remainder are deoxyribonucleotides, such a substrate is still not cleaved as efficiently as an all-RNA substrate (Yang, et al., 1990). Therefore, either there are other 2'-hydroxyl groups in the substrate that are directly involved in stabilizing the active complex, or the structure of the complex formed by the ribozyme and the predominantly DNA substrate is sufficiently different from that formed by the ribozyme with the all-RNA substrate to result in a slightly different arrangement of the crucial groups involved in the reaction. Our observation that activity does not decrease when DNA is substituted into the arms of the ribozyme indicates there are no crucial 2'-hydroxyl groups in the arms, at least in positions 1–10 and 35–42 (FIG. 5). This results is consistent with the observations of Paolella et al. (Paolella, et al., 1992) which showed complete retention of activity by a ribozyme in which all 2'-hydroxyl groups in the hybridizing arms had been replaced by 2'-O-allyl. The fact that the rate of cleavage increases with DNA in the arms of the ribozyme suggest that most likely there is a subtle change in the conformation of the resulting double-helix allowing a more favorable positioning of the critical groups involved in the cleavage reaction. Thus, it may be expected that differences between the effects of all-RNA ribozymes and analogous DNA-armed ribozymes against specific targets will vary with the sequence of the target, as the local structure and flexibility of the helices formed will depend also on the sequence.

Stability of Ribozymes in Serum

Ribozymes 1 and 2 were subjected to degradation in fetal calf serum in order to investigate their relative stabilities. At all concentrations of serum between 5% and 0.01%, no significant differences were observed. At a serum concentration of 0.1%, the half-life of both ribozymes was around 1–2 minutes. Ribozyme 1 was cleaved into small fragments with no preferred cleavage sites. Ribozyme 2, on the other hand, was initially cleaved between $G_{13}$ and $A_{14}$ and, subsequently, after $T_{10}$ to yield a 10-mer of DNA which was relatively stable and constituted >90% of the 5' end-labelled material observed on the gel after 20 minutes incubation at 0.1% serum. At higher serum concentrations and longer times to 10-mer product was degraded to a 9-mer, but no shorter fragments appeared even after 60 minutes in 5% serum. Clearly the DNA portion of ribozyme 2 is several orders of magnitude more stable than the RNA. The observation that both ribozyme 1 and ribozyme 2 are degraded in serum at the same rate, without significant degradation of the DNA portion of ribozyme 2, implies that RNA endonucleases are predominantly responsible for the degradation of this medium. In contrast, the DNA portion appears to be very slowly degraded, largely, if not exclusively, by 3' exonucleases.

Conclusions

The ribozymes described here differ in their efficiency, as measured by $k_{cat}/K_m$, by a factor of 15. The directly-measured first-order rate constants for the cleavage reactions differ only 3-fold. The discrepancy probably arises largely from different rate-determining steps for the two reactions. Under the conditions used in this study, the rate-determining step for the all-RNA ribozyme may be association with substrate, whereas for the DNA-armed ribozyme it is the cleavage reaction. The question of the rate-determining step for ribozyme 1, while interesting, does not affect the conclusions that (i) a DNA-armed ribozyme is an order of magnitude more active than its all-RNA analogue and (ii) that this difference originates, in part, in the cleavage step. If the observation holds generally, or even for a subset of ribozymes, it means that DNA-armed ribozymes will be very useful as starting molecules for the introduction of further modifications designed to protect the conserved nucleotides against nuclease attack: they possess enhanced cleavage activity and nuclease resistant hybridizing arms.

Recently, Taylor et al. (Taylor, et al., 1992) have reported data on a DNA-armed ribozyme that has 6-fold greater catalytic activity than an analogous all-RNA ribozyme, when targeted against a 28-mer RNA substrate at 55° C.

They attributed the difference in effect to the faster rate of dissociation of the cleavage products from the DNA-armed ribozyme. They also investigated the stability of the ribozymes introduced into cells with Lipofectin, and found that the DNA-armed ribozyme survived longer in cells than the all-RNA ribozyme. Our observations, that a DNA-armed ribozyme displays faster rates of cleavage and faster turnover at 30° C. compared to an all-RNA ribozyme, and the observations of Taylor et al. (Taylor, et al., 1992), of increased turnover rates on a different sequence, together imply a general usefulness for these types of molecules.

Figure 7:
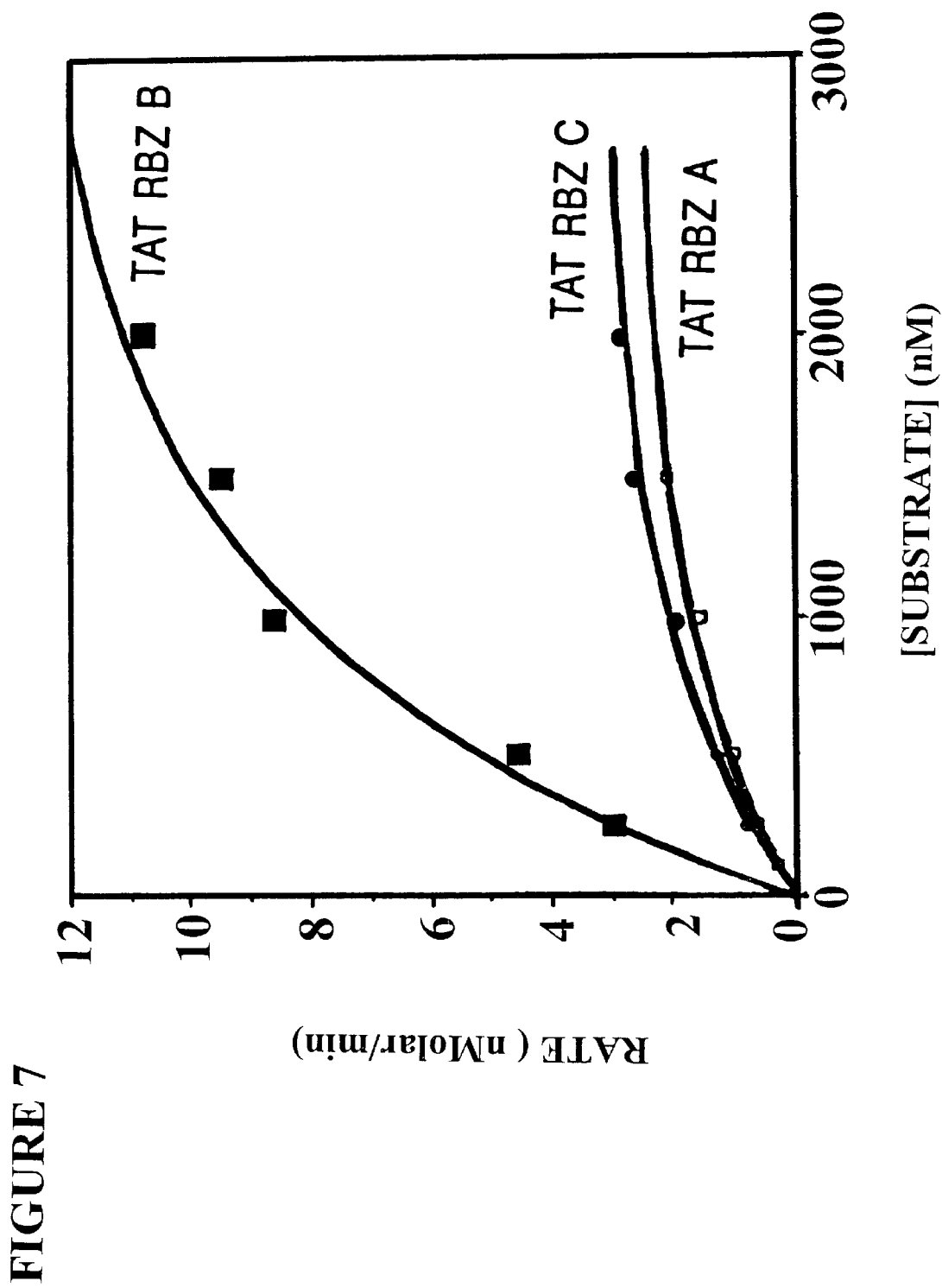
FIG. 7. The rate of cleavage by the three TAT ribozymes as a function of substrate concentration is shown. The kinetic results may be found in Table 4, TATRA (all RNA); TATRB (DNA hybridizing arms); TATRC (DNA hybridizing arms and DNA helix II).

Table 4 shows kinetic constants for DNA-armed ribozymes, compared with all-RNA ribozymes and ribozymes consisting of all DNA except for the conserved ribonucleotides. Data for TATRA, TATRB, and TATRC may be found in FIG. 7.

TABLE 4

| Ribozyme | $k_{cat}$ (min$^{-1}$) | $K_m$ (nM) | $k_{cleavage}$ (min$^{-1}$) | Temp (° C.) |
|---|---|---|---|---|
| GHRA (all RNA) | 0.4 | 38 | 1.6 | 30 |
| GHRB (DNA arms) | 8.9 | 59 | 5.0 | 30 |
| TATRA (all RNA) | 0.35 | 1084 | 0.24 | 37 |
| TATRB (DNA arms) | 1.8 | 1300 | 2.0 | 37 |
| TATRC (DNA arms + DNA helix II) | 0.45 | 1165 | — | 37 |

$k_{cat}$ and $K_m$ are from turnover kinetic experiments (ribozyme concentration very much less than substrate concentration);
$k_2$ is the rate at which substrate is cleaved, and is measured with ribozyme concentration greater than substrate concentration. kcat will equal $k_2$ if the rate-determining step in the turnover reactions is the cleavage step.

All data were obtained using substrates of 13 nucleotides; 10 mM MgCl$_2$, 50 mM Tris,Cl pH 8.0. GH is growth hormone; substrate sequence 5' GCGGGUC AUGAAG 3' (SEQ ID NO:22). TAT substrate sequence 5' GGAAGUC AGCCUA 3' (SEQ ID NO:23).

The important and unexpected observation here is that the rate of cleavage of the substrate by ribozyme is increased several-fold when DNA is in the hybridizing arms of the ribozyme, compared to an all-RNA ribozyme. (Note that we expected better stability properties when we introduced DNA into the minizyme, and that is why we continued on with the DNA-armed ribozyme experiments; however the enhanced cleavage activity we obtained with DNA-armed ribozymes was certainly not an expected result).

Figure 8:
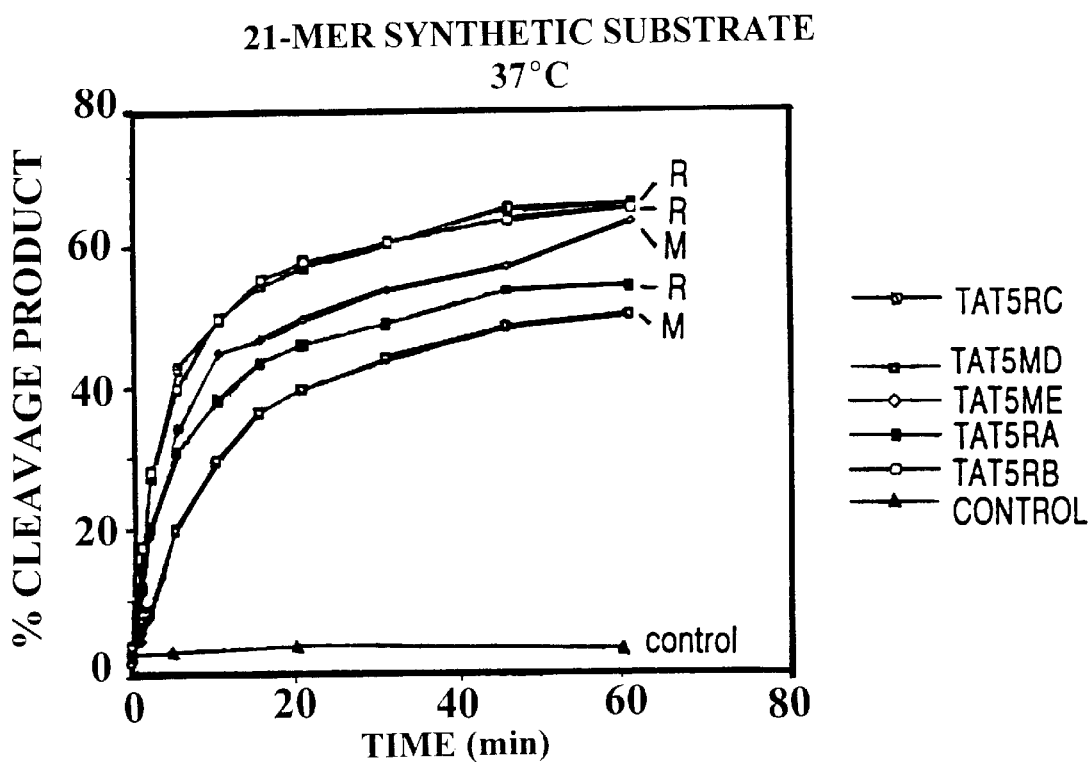
FIG. 8. The rate of cleavage of ribozymes and minizyme targeted against a short 21 bp substrate and a long 428 bp substrate where the catalyst is in excess.
Figure 8:
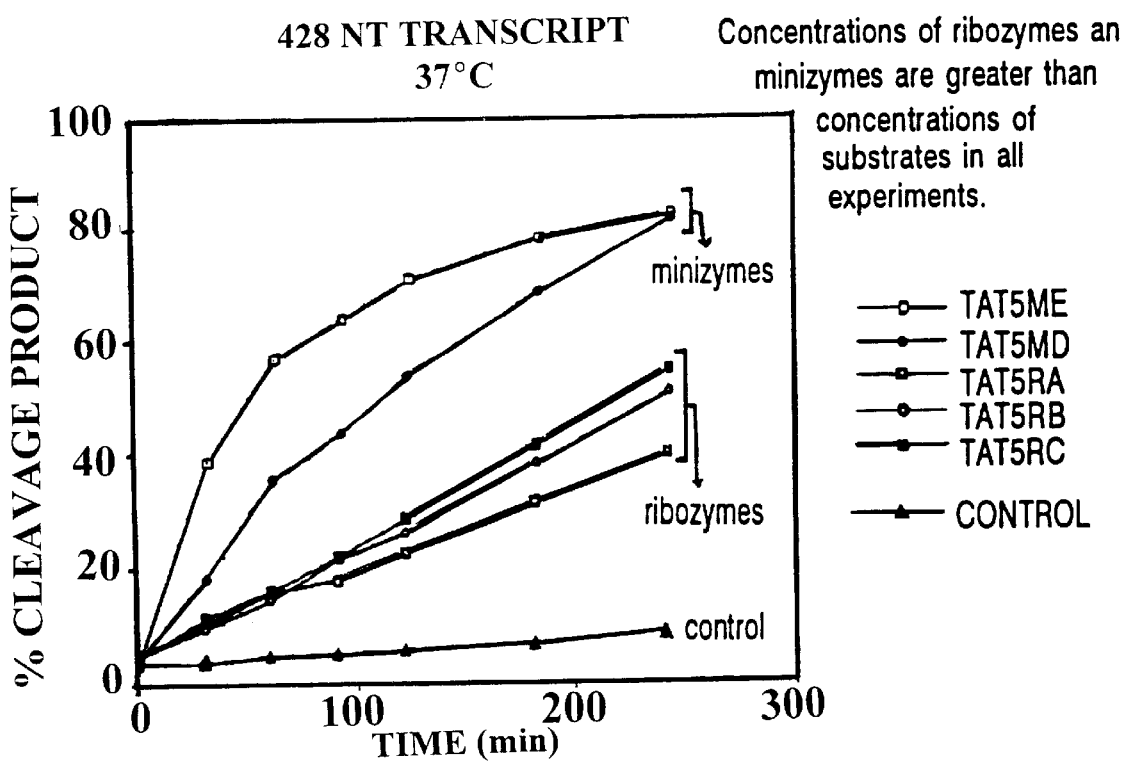

FIG. 8 shows that activity of minizymes and ribozymes against long and short substrates. Suprisingly, the minizyme is much more active against the long substrate.

Experiment 3

Number of Nucleotides in Hybridizing Arms or Ribozyme
(a) Four DNA-armed ribozymes were synthesized which were identical except for the number and sequence of the nucleotides in the hybridizing arms. In the molecules below, lower case letter represent DNA, upper case letters RNA, x+y shows the number of potential base pairs formed between the ribozyme and substrate, and the nucleotides involved in these potential base-pairs are underlined.

GHRB 5'
    gacacttcatCUGAUGAGUCCUUUUGGACGAA
    ACccgcaggt 10+10+substrate 5' ACCUGCGGGUC
    AUGAAGUGUC (SEQ ID NO:24–25)

TATRB 5'
    gtcctaggctCUGAUGAGUCCUUUUGGACGAA
    ACttcctgga 10+10+substrate 5' UUCCAGGAAGUC
    AGCCUAGGAC(SEQ ID NO:26–27)

TNFRB 5'
    aagatgatctCUGAUGAGUCCUUUUGGACGAA
    ACtscctgg 10+9+substrate 5' CCAGGCAGUC
    AGAUCAUCUU (SEQ ID NO:28–29)

ILKRB 5'caatgcaaCUGAUGAGUCCUUUUGGACGAA
    ACagga 8+6+substrate 5' UCCUGUC UUGCAUUG
    (SEQ ID NO:30–31)

Figure 9:
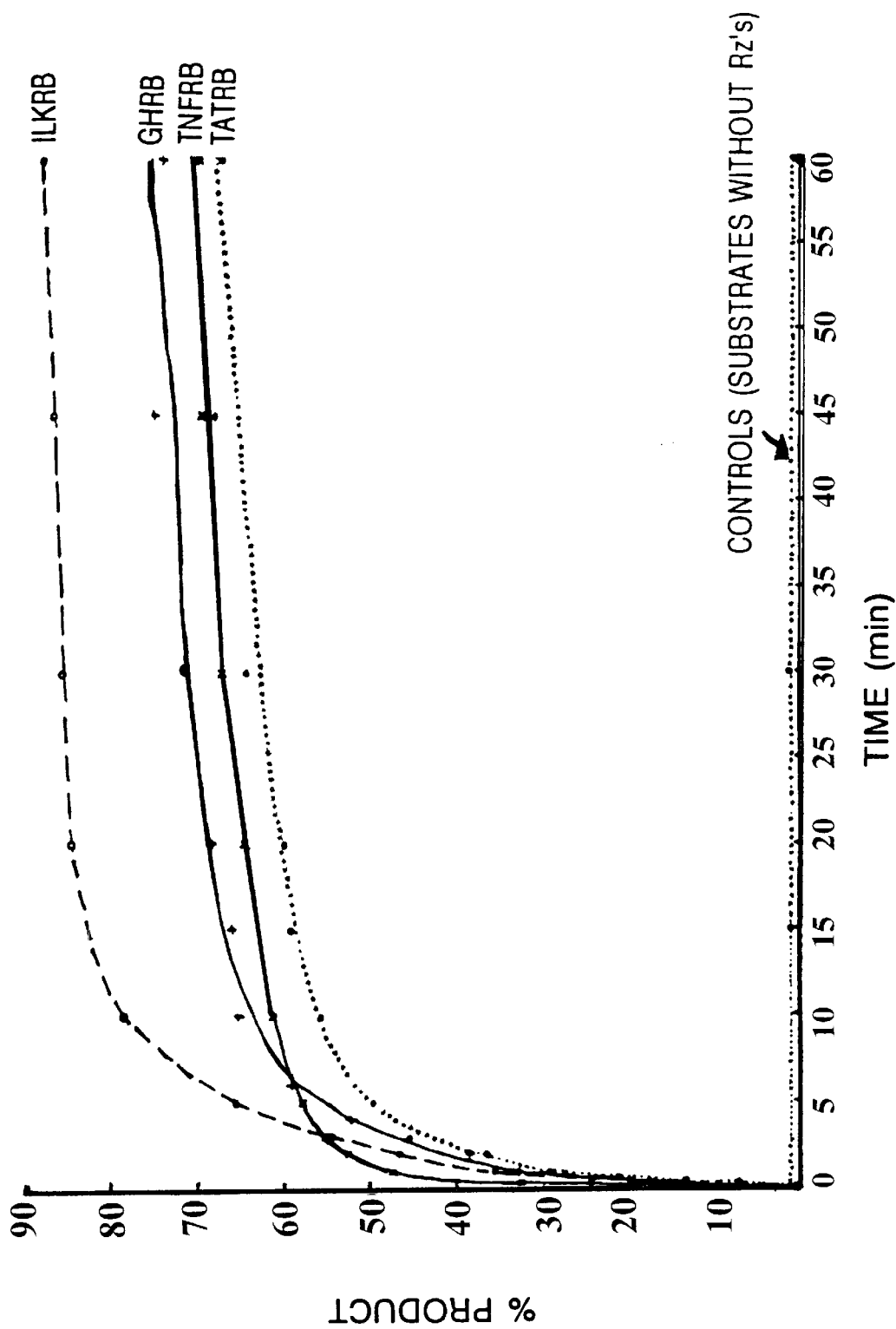
FIG. 9. The figure shows the relative rates of cleavage of DNA-armed ribozymes with varying arm lengths targetted against a variety of target genes.

The cleavage activities of these ribozymes, against their respective short substrates, are given in FIG. 9. Ribozyme is in excess over substrate; 10 mM MgCl2, 50 mM Tris.Cl, pH 8, 37° C.

(b) In addition to the cleavage activities by GHRB and TATRB against 21-nucleotide substrates shown in (a) above, we have measured cleavage activities by GHRB and TATRB against shorter, 13-nucleotide substrates. The substrate sequences (SEQ ID No.:22–23) are
    GH 5' GCGGGUC AUGAAG
    TAT 5' GGAAGUC AGCCUA, and so these provide two examples of 6+6 base pairs formed between DNA-armed ribozyme and RNA substrate.

Figure 10:
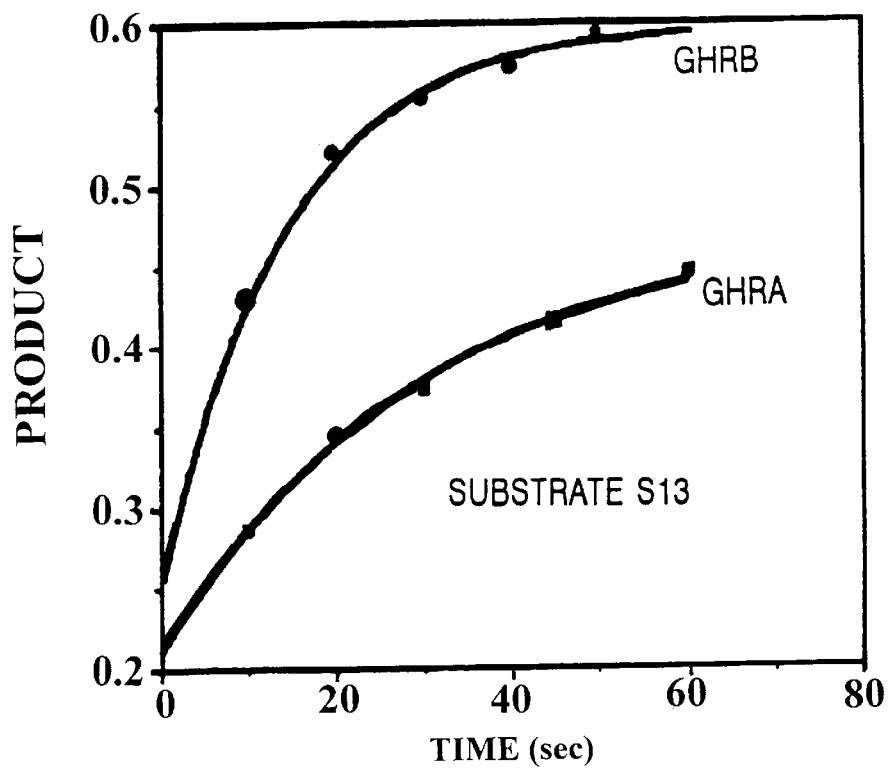
FIG. 10. The figure shows the relative rates of cleavage of DNA-armed ribozymes versus all RNA ribozymes against a short 13 bp substrate. GHRA and GHRB are growth hormone RNA ribozyme and DNA-armed ribozyme respectively.
Figure 10:
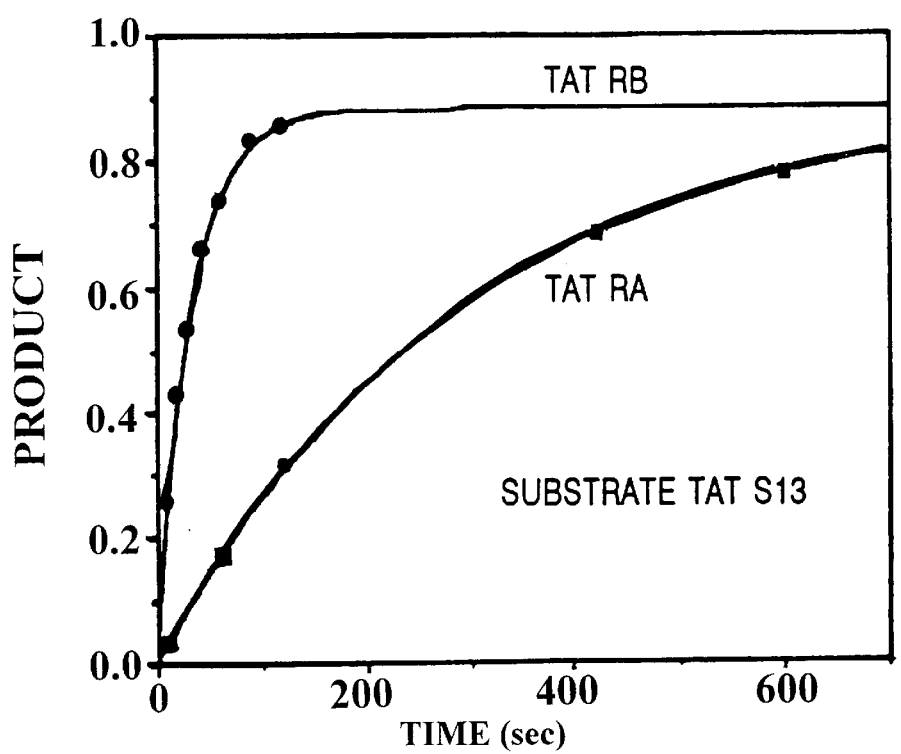

The cleavage activities against the shorter substrates are shown in FIG. 10, with data for the analogous all-RNA ribozymes (GHRA and TATRA) also included. For reasons we do not yet understand, both GHRB and TATRB cleave their respective 13-mer substrates faster than their 21-mer substrates.

3. Number of Base Pairs in Stem of Helix II

In addition to the minizyme which has zero b.p. in helix II, we have DNA-armed ribozymes which are identical in every way except for the number of base pairs in helix II; and we have examples of 2, 4 or 8 b.p. in helix II. In the molecules below, the nucleotides involved in base-pairs in helix II are underlined. TATRB-H4 (below) is identical to TATRB (above)(SEQ ID NO:34–35). (See FIG. 11)

TATRB-H2
5'gtcctaggctCUGAUGA<u>GC</u>UUUU<u>GC</u>GAAACttcctgga

Figure 12:
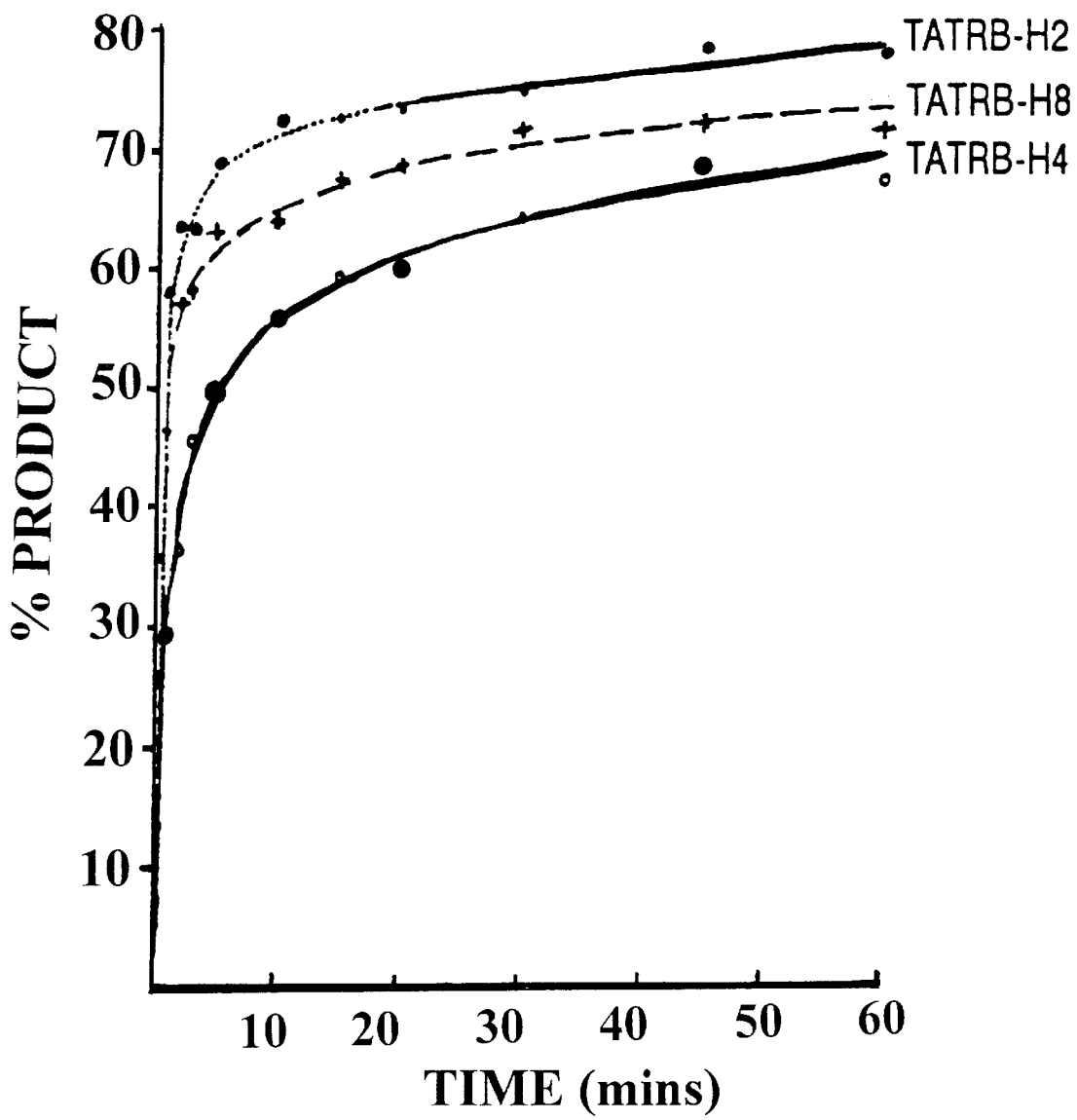
FIG. 12. The figure shows the activity of three DNA-armed ribozymes with varying stem length against a short (21 bp) TAT substrate at 37° C.
Figure 13:
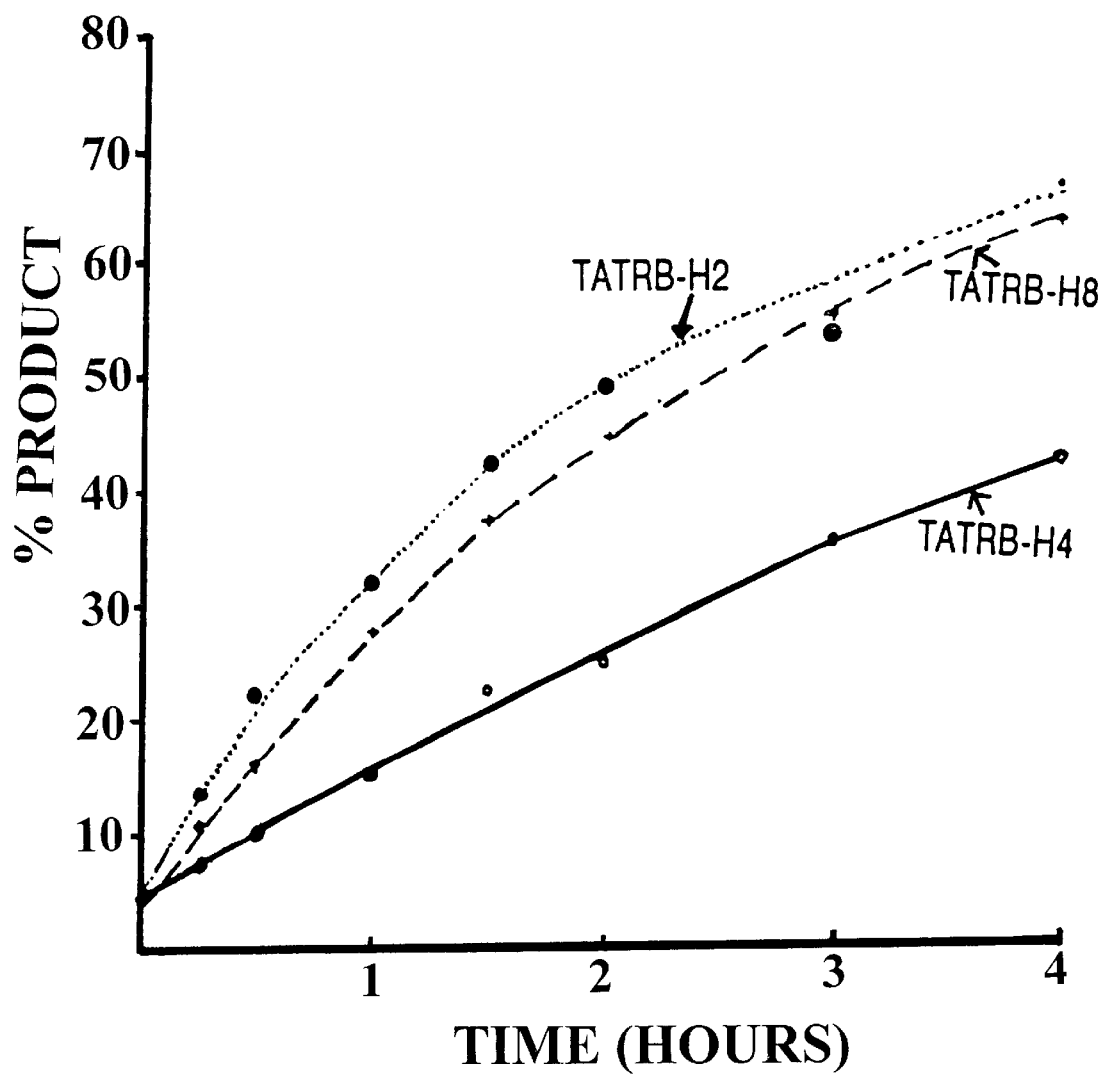
FIG. 13. The figure shows the activity of three DNA-armed ribozymes with varying stem length against a long (428 bp) TAT substrate at 37° C.

TATRB-H4
5'        gtcctaggctCUGAUGA<u>GUCC</u>UUUU
    <u>GGAC</u>GAAACttcctgga TATRB-H8
5'        gtcctaggctCUGAUGA<u>GUCCGUCC</u>UUUU
    <u>GGACGGAC</u>GAAACttcctgga The cleavage activities of these ribozymes against the same short substrate is shown in FIG. 12, and that against a longer transcribed substrate which contains the target sequence is shown in FIG. 13.

4 DNA-armed Ribozymes with Modified Nucleotides are Shown in FIG. 14

TATRBPS is similar to TATRB above, except that phosphates are replaced by phosphorotioates in the stem-loop of helix II (shown by capital letter in italics).

Figure 15:
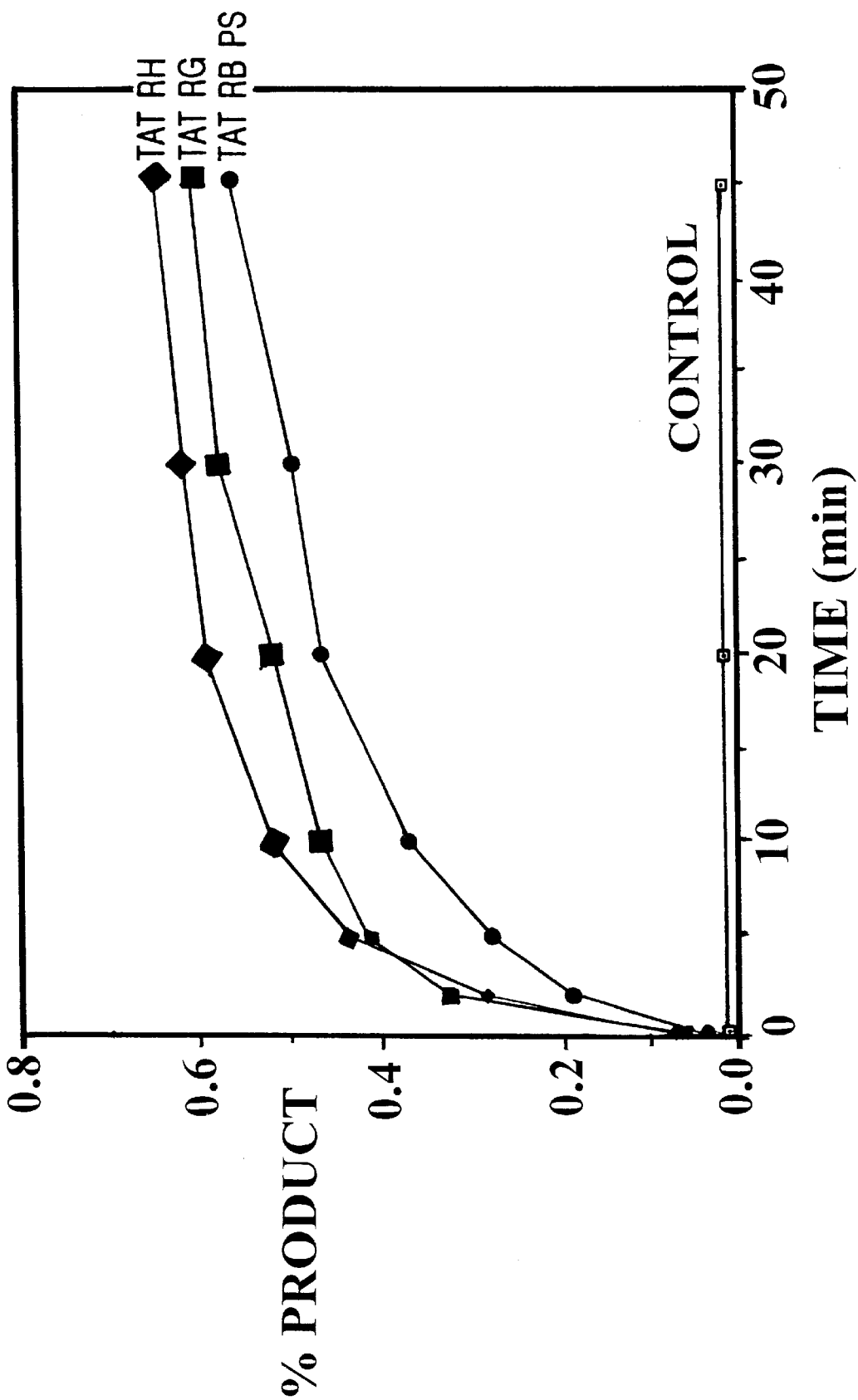
FIG. 15. The activity of the three mixed DNA RNA ribozymes against a TAT substrate is shown.

The activity of this ribozyme, relative to TATRG and TATRH, is shown in FIG. 15.

5. Increased Stability in Cells

There is data that DNA-armed ribozymes are much more stable in cells than all RNA ribozymes (Taylor, et al., 1992).

REFERENCES

Altman, S., Baer, M., Gold, H., Guerrier-Takada, C., Kirsebom, L., Lawrence, N., Lumelsky, N. & Vioque, A. (1987) in Molecular Biology of RNA: New Perspectives, eds. Inouye, M. & Dudock, B.S. Academic, London, pp. 3–15.

Buzayan, J. M., Gerlach, W. L. & Bruening, G. (1986) Nature (London) 323:349–353.

Calladine, C. R., Collis, C. M., Drew, H. R. & Mott, M. (1991) J. Mol. Biol. 221:981–1005.

Cameron, F. H. & Jennings, P. A. (1989) Proc. Natl. Acad. Sci. USA 86:9139–9143.

Cech, T. R. & Bass, B. L. (1986) Annu. Rev. Biochem. 55, 599–629.
Chrisley, L. A. (1991) Antisense Research and Development, 1:65–113.
Cotten, M. & Birnstiel, M. L. (1989) EMBO J. 8:3861–3866.
Dahm, S. C. & Uhlenbeck, O. C. (1990) Biochime. 72, 819–823.
Diekmann, S. & Wang, J. C. (1985) J. Mol. Biol. 186:1–11.
Egholm, (1992) J. Am. Chem. Soc. 114:1895.
Forster, A. C., Davies, C., Sheldon, C. C., Jeffries, A. C. & Symons, R. H. (1988) Nature (London) 334:265–267.
Forster, A. C. & Symons, R. H. (1987) Cell, 50:9–16.
Forster, A. C. & Symons, R. H. (1987) Cell 49:211–220.
Gast, F.-U. & Hagerman, P. J. (1991) Biochemistry 30:4268–4277.
Goodchild, J. & Kohli, V. (1991) Arch. Biochem. Biophys. 284:386–391.
Hampel et al. Nuc. Acids Res. (1990) 18:299–304.
Hanvey et al., (1992) Science Vol. 258:1409–1548.
Haseloff, J. & Gerlach, W. L. (1988) Nature (London) 334:585–591.
Jeffries, A. C., Symons, R. H. (1989) Nucleic Acids Res. 17:1371–1377.
Koizumi, M., Iwai, S. & Ohtsuka, E. (1988) FEBS Lett., 239:285–288.
McCall, M. J., Hendry, P. & Jennings, P. A. (1992) Proc. Natl. Acad. Sci. USA, 89:5710–5714.
McCall, M. J., Brown, T. & Kennard, O. (1985) J. Mol. Biol. 183:385–396.
Nielson, (1991) Science 254:1497.
Olsen, D. B., Benseler, F., Aurup, H., Pieken, W. A., & Eckstein, F. (1991) Biochemistry 30:9735–9741.
Paolella, G., Sproat, B. S. & Lamond, A. I. (1992) EMBO J., 11:1913–1919.
Perreault, J.-P., Wu, T., Cousineau, B., Ogilvie, K. K. & Cedergren, R. (1990) Nature, 344:565–567.
Perreault, J.-P., Labuda, D., Usman, N., Yang, J.-H., & Cedergren, R. (1991) Biochemistry 30:4020–4025.
Pieken, W. A., Olsen, D. B., Benseler, F., Aurup, H. & Eckstein, R. (1991) Science, 253:314–317.
Prody, G. A., Bakos, J. T., Buzayan, J. M., Schneider, I. R. & Bruening, G. (1986) Science 231:1577–1580.
Ruffner, D. E., Stormo, G. D. & Uhlenbeck, O. C. (1990) Biochemistry 29:10695–10702.
Saenger, W. (1984) Principles of Nucleic Acid Structure (Springer, N.Y.).
Sarver, N., Cantin, E., Chang, P., Zala, J., Ladna, P., Stephens, D. & Rossi, J. (1990) Science 247:1222–1225.
Saxena, S. L. & Ackerman, E. J. (1990) J. Biol. Chem. 265:17106–17109.
Sioud, M. & Drlica, K. (1991) Proc. Natl. Acad. Sci. USA 88:7303–7307.
Sioud, M., Natvig, J. B., & Førre, Ø. (1992) J. Mol. Biol. 223:831–835.
Steinecke, P., Herget, T & Schreier, P. H. (1992) EMBO J., 11:1525–1530.
Strobel, S. A., et al., (1991) Nature 350:172–174.
Taylor, N. R., Kaplan, B. E., Swiderski, P., Li, H., & Rossi, J. J. (1992) Nucleic Acids Res. 20:4559–4565.
Uhlenbeck, O. C. (1987) Nature (London) 328:596–600.
Uhlmann, E. and Peyman, A., (1990) Chemical Reviews 90:543–584.
Williams, D. M., Pieken, W. A. & Eckstein, F. (1992) Proc. Natl. Acad. Sci. USA 89:918–921.
Yang, J.-H., Perreault, J.-P., Labuda, D., Usman, N., & Cedergren, R. (1990) Biochemistry 29:11156–11160.

What is claimed is:

1. A compound having the structure:

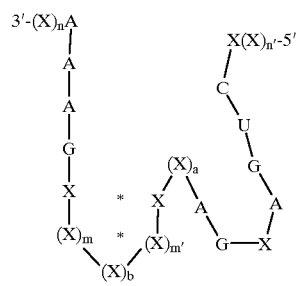

wherein each X represents a ribonucleotide or a deoxyribonucleotide, which is the same or different and may be modified or substituted in its sugar, phosphate or base;

wherein each x represents a nucleotide which may be modified or substituted in its sugar, phosphate or base;

wherein each of A, C, U, and G represents a different ribonucleotide which may be modified in its sugar, phosphate or base;

wherein at least one nucleotide is modified or substituted in its sugar;

wherein each of $(x)_n$ and $(x)_{n'}$ represents an oligonucleotide having a predetermined sequence sufficiently complementary to a predefined RNA target sequence to allow hybridization to the RNA target sequence and each of n and n' represents an integer which defines the number of nucleotides in the oligonucleotide with the proviso that the sum of n+n' is sufficient to allow the compound to hybridize with the RNA target sequence;

wherein each * represents base pairing between the nucleotides located on either side thereof;

wherein each solid line represents a chemical linkage providing covalent bonds between the nucleotides located on either side thereof;

wherein a represents an integer which defines a number of nucleotides with the proviso that a may be 0 or 1 and if 0, the A located 5' of $(X)_a$ is bonded to the X located 3' of $(X)_a$;

wherein each of m and m' represents 0 or an integer which is greater than or equal to 1; and wherein $(X)_b$ represents an oligonucleotide and b represents an integer which is greater than or equal to 2.

2. The compound of claim 1, wherein each of m and m' are one and b is four.

3. The compound of claim 1, wherein each of m and m' are seven and b is four.

4. The compound of claim 1, wherein $(x)_n$ or $(x)_{n'}$ represents an oligodeoxyribonucleotide.

5. The compound of claim 1, wherein $(x)_n$ and $(x)_{n'}$ represent oligodeoxyribonucleotides.

6. The compound of claim 1, wherein each X represents a ribonucleotide.

7. The compound of claim 1, wherein each X represents a deoxyribonucleotide.

8. The compound of claim 1 having the structure:

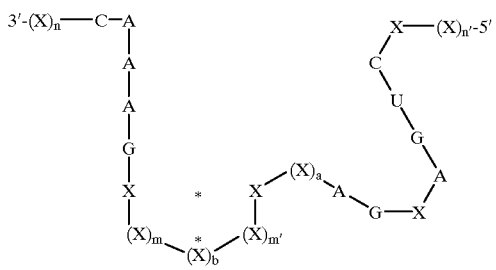

wherein each X represents a ribonucleotide or a deoxyribonucleotide, which is the same or different and may be modified or substituted in its sugar, phosphate or base:

wherein each x represents a nucleotide which may be modified or substituted in its sugar, phosphate or base;

wherein each of A, C, U, and G represents a different ribonucleotide which may be modified in its sugar, phosphate or base;

wherein c represents a cytosine nucleotide which may be modified or substituted in its sugar, phosphate or base;

wherein at least one nucleotide is modified or substituted in its sugar;

wherein each of $(x)_n$ and $(x)_{n'}$ represents an oligonucleotide having a predetermined sequence sufficiently complementary to a predefined RNA target sequence to allow hybridization to the RNA target sequence and each of n and n' represents an integer which defines the number of nucleotides in the oligonucleotide with the proviso that the sum of n+n' is sufficient to allow the compound to hybridize with the RNA target sequence;

wherein each * represents base pairing between the nucleotides located on either side thereof;

wherein each solid line represents a chemical linkage providing covalent bonds between the nucleotides located on either side thereof;

wherein a represents an integer which defines a number of nucleotides with the proviso that a may be 0 or 1 and if 0, the A located 5' of $(X)_a$ is bonded to the X located 3' of $(X)_a$;

wherein each of m and m' represents 0 or an integer which is greater than or equal to 1; and wherein $(X)_b$ represents an oligonucleotide and b represents an integer which is greater than or equal to 2.

9. The compound of claim 8, wherein each of m and m' are one and b is four.

10. The compound of claim 8, wherein each of m and m' are seven and b is four.

11. The compound of claim 8, wherein $(x)_n$ or $(x)_{n'}$ represents an oligodeoxyribonucleotide.

12. The compound of claim 8, wherein $(x)_n$ and $(x)_{n'}$ represent oligodeoxyribonucleotides.

13. The compound of claim 8, wherein each X represents a ribonucleotide.

14. The compound of claim 8, wherein each X represents a deoxyribonucleotide.

15. A compound having the structure:

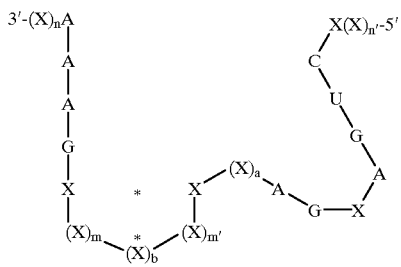

wherein each X represents a ribonucleotide or a deoxyribonucleotide, which is the same or different and may be modified or substituted in its sugar, phosphate or base;

wherein each x represents a nucleotide which may be modified or substituted in its sugar, phosphate or base;

wherein at least one nucleotide represented by X or x is modified or substituted in its sugar;

wherein each of A, C, U, and G represents a different ribonucleotide;

wherein each of $(x)_n$ and $(x)_{n'}$ represents an oligonucleotide having a predetermined sequence sufficiently complementary to a predefined RNA target sequence and each of n and n' represents an integer which defines the number of nucleotides in the oligonucleotide with the proviso that the sum of n+n' is sufficient to allow the compound to hybridize with the RNA target sequence;

wherein each * represents base pairing between the nucleotides located on either side thereof;

wherein each solid line represents a chemical linkage providing covalent bonds between the nucleotides located on either side thereof;

wherein a represents an integer which defines a number of nucleotides with the proviso that a may be 0 or 1 and if 0, the A located 5' of $(X)_a$ is bonded to the X located 3' of $(X)_a$;

wherein each of m and m' represents 0 or an integer which is greater than or equal to 1; and wherein $(X)_b$ represents an oligonucleotide and b represents an integer which is greater than or equal to 2.

16. The compound of claim 15, wherein each of m and m' are one and b is four.

17. The compound of claim 15, wherein each of m and m' are seven and b is four.

18. The compound of claim 15, wherein $(x)_n$ or $(x)_{n'}$ represents an oligodeoxyribonucleotide.

19. The compound of claim 15 having the structure:

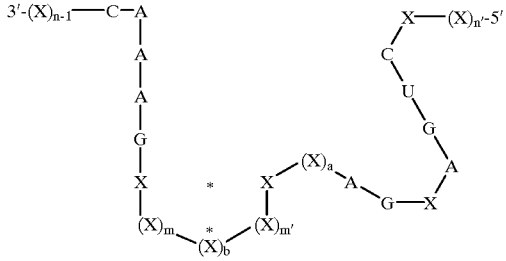

wherein each X represents a ribonucleotide or a deoxyribonucleotide, which is the same or different and may be modified or substituted in its sugar, phosphate or base;

wherein each x represents a nucleotide which may be modified or substituted in its sugar, phosphate or base;

wherein c represents a cytosine nucleotide which may be modified or substituted in its sugar, phosphate or base;

wherein at least one nucleotide represented by X or x is modified or substituted in its sugar;

wherein each of A, C, U, and G represents a different ribonucleotide;

wherein each of $(x)_n$ and $(x)_{n'}$ represents an oligonucleotide having a predetermined sequence sufficiently complementary to a predefined RNA target sequence to allow hybridization to the RNA target sequence and each of n and n' represents an integer which defines the number of nucleotides in the oligonucleotide with the proviso that the sum of n+n' is sufficient to allow the compound to hybridize with the RNA target sequence;

wherein each * represents base pairing between the nucleotides located on either side thereof;

wherein each solid line represents a chemical linkage providing covalent bonds between the nucleotides located on either side thereof;

wherein a represents an integer which defines a number of nucleotides with the proviso that a may be 0 or 1 and if 0, the A located 5' of $(X)_a$ is bonded to the X located 3' of $(X)_a$;

wherein each of m and m' represents 0 or an integer which is greater than or equal to 1; and wherein $(X)_b$ represents an oligonucleotide and b represents an integer which is greater than or equal to 2.

20. The compound of claim 19, wherein each of m and m' are one and b is four.

21. The compound of claim 19, wherein $(x)_n$ or $(x)_{n'}$ represents an oligodeoxyribonucleotide.

22. The compound of claim 1, wherein each at least one nucleotide in the compound is a 2'-methoxyribonucleotide.

23. The compound of claim 1, wherein each at least one nucleotide in the compound is a a-anomer of the nucleotide.

24. The compound of claim 1, wherein the 3' end of the oligonucleotide $(x)_n$ and/or the 5' end of the oligonucleotide $(x)_{n'}$ contain a blocking group which is resistant to nuclease attack.

25. The compound of claim 24, wherein the blocking group is selected from the group consisting of optionally substituted alkyl, optionally substituted phenyl, optionally substituted alkanoyl, phosphorothioate, phosphoroamidate or methyl phosphonate nucleotide analogues which are resistant to nuclease attack, spermine, and spermidine.

26. The compound of claim 15, wherein each at least one nucleotide in the compound is a 2'-methoxyribonucleotide.

27. The compound of claim 15, wherein each at least one nucleotide in the compound is a a-anomer of the nucleotide.

28. The compound of claim 15, wherein the 3' end of the oligonucleotide $(x)_n$ and/or the 5' end of the oligonucleotide $(x)_{n'}$ contain a blocking group which is resistant to nuclease attack.

29. The compound of claim 28, wherein the blocking group is selected from the group consisting of optionally substituted alkyl, optionally substituted phenyl, optionally substituted alkanoyl, phosphorothioate, phosphoroamidate or methyl phosphonate nucleotide analogues which are resistant to nuclease attack, spermine, and spermidine.

* * * * *

UNITED STATES PATENT AND TRADEMARK OFFICE
CERTIFICATE OF CORRECTION

PATENT NO. : 6,365,730 B1
DATED : April 2, 2002
INVENTOR(S) : Philip Anthony Jennings, Maxine June McCall and Philip Hendry It is certified that error appears in the above-identified patent and that said Letters Patent is hereby corrected as shown below:

Title page,
Item [54], "DNA-ARMED RIBOZYMES AND MINIZYMES" should read
-- MODIFIED RIBOZYMES --

Column 2,
Line 36, "MM MgCl$_2$" should read -- mM MgCl$_2$ --

Column 5,
Lines 17-30, should read

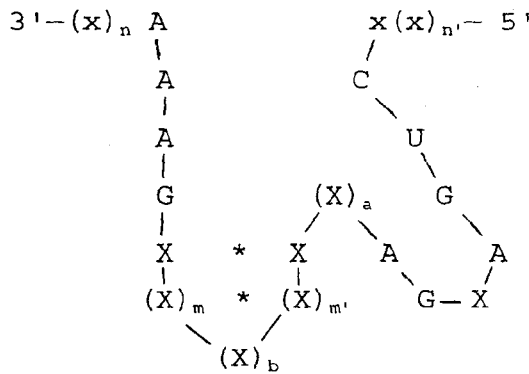

Line 46, "sequence it is not mandatory" should read -- sequence but it is not mandatory --
Line 53, "prefereably" should read -- preferably --

Column 6,
Lines 59-60, "phgosphorothioate" should read -- phosphotothioate --

Column 8,
Line 15, "glycosyl $C_1$ -N link" should read -- glycosyl $C_{1'}$ -N link --

Column 10,
Lines 37-38, "that one" should read -- that when one --

Column 11,
Line 15, "which may be" should read -- which may be ameliorated are --

Column 13,
Line 34, "the Na$^+$ from" should read -- the Na$^+$ form --

UNITED STATES PATENT AND TRADEMARK OFFICE
CERTIFICATE OF CORRECTION

PATENT NO. : 6,365,730 B1
DATED : April 2, 2002
INVENTOR(S) : Philip Anthony Jennings, Maxine June McCall and Philip Hendry It is certified that error appears in the above-identified patent and that said Letters Patent is hereby corrected as shown below:

Column 17,
Line 53, "data do not following this relation ship" should read -- data do not follow this relationship --
Line 61, "marker i lane 1." should read -- marker in lane 1 --

Column 20,
Line 4, "T, $8.8 \times 10_3$" should read -- T, $8.8 \times 10^3$ --
Line 41, "tine" should read -- time --
Lines 41 and 46, "$P_{28}$" should read -- $P_\infty$ --
Line 52, "ribocytodine" should read -- ribocytidine --

Column 21,
Line 9, "replace" should read -- replaced --

Column 22,
Line 26, "suggest" should read -- suggests --
Lines 34 and 40, "kcat" should read -- $k_{cat}$ --

Column 23,
Line 7, "Km's" should read -- $K_m$'s --
Line 41, "for the degradation of this medium" should read -- for the degradation in this medium --

Column 25,
Table 4, line 4 of explanation, "kcat" should read -- $k_{cat}$ --

Column 26,
Line 1, "Actscctgg" should read -- Actgcctgg --
Line 8, "MgCl2" should read -- $MgCl_2$ --
Line 46, "4" should read -- 4. --
Line 47, "FIG. 14" should read -- FIG. 14. --
Line 49, "phosphorotioates" should read -- phosphorothioates --

UNITED STATES PATENT AND TRADEMARK OFFICE
CERTIFICATE OF CORRECTION

PATENT NO. : 6,365,730 B1
DATED : April 2, 2002
INVENTOR(S) : Philip Anthony Jennings, Maxine June McCall and Philip Hendry It is certified that error appears in the above-identified patent and that said Letters Patent is hereby corrected as shown below:

Column 41,
Lines 2-17, should read as follows:

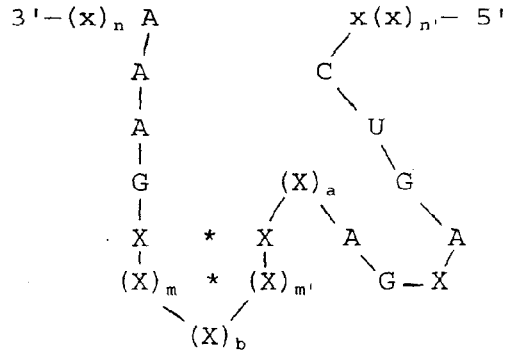

Column 42,
Lines 2-15, should read as follows:

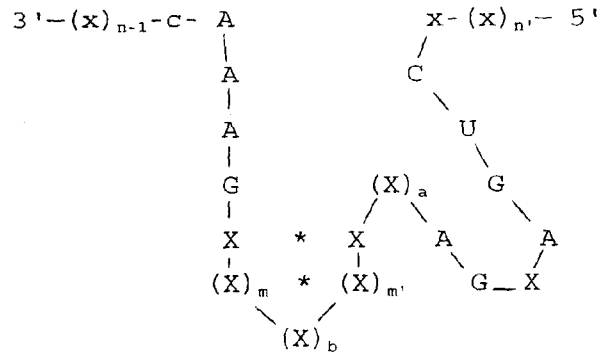

Column 43,
Lines 2-15, should read as follows:

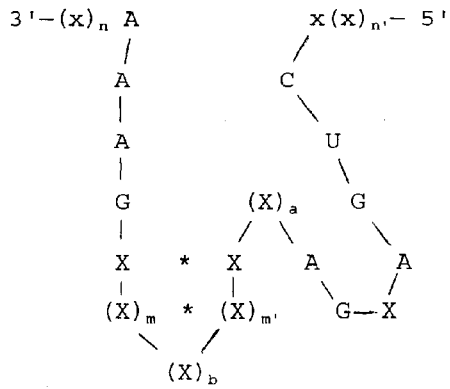

UNITED STATES PATENT AND TRADEMARK OFFICE
CERTIFICATE OF CORRECTION

PATENT NO. : 6,365,730 B1
DATED : April 2, 2002
INVENTOR(S) : Philip Anthony Jennings, Maxine June McCall and Philip Hendry It is certified that error appears in the above-identified patent and that said Letters Patent is hereby corrected as shown below:

<u>Column 43 (cont'd),</u>
Lines 51-63, should read as:

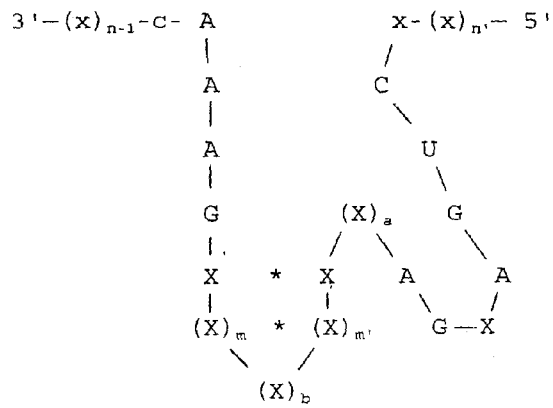

<u>Column 44,</u>
Lines 41 and 55, "a a-anomer" should read -- an α-anomer --

Signed and Sealed this

Fifteenth Day of July, 2003

JAMES E. ROGAN
*Director of the United States Patent and Trademark Office*

SEQUENCE LISTING (1) GENERAL INFORMATION:

(iii) NUMBER OF SEQUENCES: 31

(2) INFORMATION FOR SEQ ID NO:1:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: RNA (genomic)

(xi) SEQUENCE DESCRIPTION: SEQ ID NO:1:

ACCUGCGGGU CAUGAAGUGU                    20

(2) INFORMATION FOR SEQ ID NO:2:

(i) SEQUENCE CHARACTERISTICS:
      (A) LENGTH: 42 base pairs
      (B) TYPE: nucleic acid
      (C) STRANDEDNESS: single
      (D) TOPOLOGY: linear (ii) MOLECULE TYPE: Other nucleic acid
      (A) DESCRIPTION: (Mixed DNA/RNA oligomer
         see specification and figures for details)

(xi) SEQUENCE DESCRIPTION: SEQ ID NO:2:

GACACUUCAU CUGAUGAGUC CUUUUGGACG AAACCCGCAG GT         42

(2) INFORMATION FOR SEQ ID NO:3:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: Other nucleic acid
        (A) DESCRIPTION: (Mixed DNA/RNA oligomer
            see specification and figures for details)

(xi) SEQUENCE DESCRIPTION: SEQ ID NO:3:

```
GACACUUCAU CUGAUGAGAA ACCCGCAGGT                                    30
```

(2) INFORMATION FOR SEQ ID NO:4:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: Other nucleic acid
        (A) DESCRIPTION: (Mixed DNA/RNA oligomer
            see specification and figures for details)

(xi) SEQUENCE DESCRIPTION: SEQ ID NO:4:

```
GACACUUCAU CUGAUGAUUU UGAAACCCGC AGGT                               34
```

(2) INFORMATION FOR SEQ ID NO:5:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: Other nucleic acid
        (A) DESCRIPTION: (Mixed DNA/RNA oligomer
            see specification and figures for details)

(xi) SEQUENCE DESCRIPTION: SEQ ID NO:5:

```
GACACTTCAT CUGAUGAUUU UGAAACCCGC AGGT                               34
```

(2) INFORMATION FOR SEQ ID NO:6:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: Other nucleic acid
        (A) DESCRIPTION: (Mixed DNA/RNA oligomer
            see specification and figures for details)

(xi) SEQUENCE DESCRIPTION: SEQ ID NO:6:

```
GACACTTCAT CUGAUGATTT TGAAACCCGC AGGT                               34
```

(2) INFORMATION FOR SEQ ID NO:7:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (ii) MOLECULE TYPE: RNA (genomic)

```
        (xi) SEQUENCE DESCRIPTION: SEQ ID NO:7:

GGUUUACCUG CGGGUCAUGA AGUGUCUUCG GACACUUCAU CUGAUGAUUU UGAAACCCGC        60

AGGU                                                                    64

(2) INFORMATION FOR SEQ ID NO:8:

(i) SEQUENCE CHARACTERISTICS:
           (A) LENGTH: 21 base pairs
           (B) TYPE: nucleic acid
           (C) STRANDEDNESS: single
           (D) TOPOLOGY: linear (ii) MOLECULE TYPE: RNA (genomic)

(xi) SEQUENCE DESCRIPTION: SEQ ID NO:8:

AUUUGCGAGU CCACACUGGA G                                                 21

(2) INFORMATION FOR SEQ ID NO:9:

(i) SEQUENCE CHARACTERISTICS:
           (A) LENGTH: 21 base pairs
           (B) TYPE: nucleic acid
           (C) STRANDEDNESS: single
           (D) TOPOLOGY: linear (ii) MOLECULE TYPE: Other nucleic acid
           (A) DESCRIPTION: (Mixed DNA/RNA oligomer
               see specification and figures for details)

(xi) SEQUENCE DESCRIPTION: SEQ ID NO:9:

ACCTGCGGGT CATGAAGTGT C                                                 21

(2) INFORMATION FOR SEQ ID NO:10:

(i) SEQUENCE CHARACTERISTICS:
           (A) LENGTH: 13 base pairs
           (B) TYPE: nucleic acid
           (C) STRANDEDNESS: single
           (D) TOPOLOGY: linear (ii) MOLECULE TYPE: RNA (genomic)

(xi) SEQUENCE DESCRIPTION: SEQ ID NO:10:

GCGGGUCAUG AAG                                                          13

(2) INFORMATION FOR SEQ ID NO:11:

(i) SEQUENCE CHARACTERISTICS:
           (A) LENGTH: 42 base pairs
           (B) TYPE: nucleic acid
           (C) STRANDEDNESS: single
           (D) TOPOLOGY: linear (ii) MOLECULE TYPE: Other nucleic acid
           (A) DESCRIPTION: (Mixed DNA/RNA oligomer
               see specification and figures for details)

(xi) SEQUENCE DESCRIPTION: SEQ ID NO:11:

GACACUUCAU CUGAUGAGUC CUUUUGGACG AAACCCGCAG GT                          42

(2) INFORMATION FOR SEQ ID NO:12:

(i) SEQUENCE CHARACTERISTICS:
           (A) LENGTH: 42 base pairs
           (B) TYPE: nucleic acid
           (C) STRANDEDNESS: single
           (D) TOPOLOGY: linear
```

(ii) MOLECULE TYPE: Other nucleic acid
            (A) DESCRIPTION: (Mixed DNA/RNA oligomer
                see specification and figures for details)

(xi) SEQUENCE DESCRIPTION: SEQ ID NO:12:

GACACTTCAT CUGAUGAGUC CUUUUGGACG AAACCCGCAG GT                             42

(2) INFORMATION FOR SEQ ID NO:13:

(i) SEQUENCE CHARACTERISTICS:
            (A) LENGTH: 38 base pairs
            (B) TYPE: nucleic acid
            (C) STRANDEDNESS: single
            (D) TOPOLOGY: linear (ii) MOLECULE TYPE: Other nucleic acid
            (A) DESCRIPTION: (Mixed DNA/RNA oligomer
                see specification and figures for details)

(xi) SEQUENCE DESCRIPTION: SEQ ID NO:13:

GTCCTAGGCT CUGAUGAGCU UUUGCGAAAC TTCCTGGA                                  38

(2) INFORMATION FOR SEQ ID NO:14:

(i) SEQUENCE CHARACTERISTICS:
            (A) LENGTH: 42 base pairs
            (B) TYPE: nucleic acid
            (C) STRANDEDNESS: single
            (D) TOPOLOGY: linear (ii) MOLECULE TYPE: Other nucleic acid
            (A) DESCRIPTION: (Mixed DNA/RNA oligomer
                see specification and figures for details)

(xi) SEQUENCE DESCRIPTION: SEQ ID NO:14:

GTCCTAGGCT CUGAUGAGUC CUUUUGGACG AAACTTCCTG GA                             42

(2) INFORMATION FOR SEQ ID NO:15:

(i) SEQUENCE CHARACTERISTICS:
            (A) LENGTH: 50 base pairs
            (B) TYPE: nucleic acid
            (C) STRANDEDNESS: single
            (D) TOPOLOGY: linear (ii) MOLECULE TYPE: Other nucleic acid
            (A) DESCRIPTION: (Mixed DNA/RNA oligomer
                see specification and figures for details)

(xi) SEQUENCE DESCRIPTION: SEQ ID NO:15:

GTCCTAGGCT CUGAUGAGUC CGUCCUUUUG GACGGACGAA ACTTCCTGGA                     50

(2) INFORMATION FOR SEQ ID NO:16:

(i) SEQUENCE CHARACTERISTICS:
            (A) LENGTH: 42 base pairs
            (B) TYPE: nucleic acid
            (C) STRANDEDNESS: single
            (D) TOPOLOGY: linear (ii) MOLECULE TYPE: Other nucleic acid
            (A) DESCRIPTION: (Mixed DNA/RNA oligomer
                see specification and figures for details)

(xi) SEQUENCE DESCRIPTION: SEQ ID NO:16:

GTCCTAGGCT CUGAUGAGUC CUUUUGGACG AAACTTCCTG GA                             42

(2) INFORMATION FOR SEQ ID NO:17:

(i) SEQUENCE CHARACTERISTICS:
            (A) LENGTH: 42 base pairs
            (B) TYPE: nucleic acid
            (C) STRANDEDNESS: single
            (D) TOPOLOGY: linear (ii) MOLECULE TYPE: Other nucleic acid
            (A) DESCRIPTION: (Mixed DNA/RNA oligomer
                see specification and figures for details)

(xi) SEQUENCE DESCRIPTION: SEQ ID NO:17:

GUCCUAGGCU CUGAUGAGTG GTTTTCCACG AAACUUCCUG GA                            42

(2) INFORMATION FOR SEQ ID NO:18:

(i) SEQUENCE CHARACTERISTICS:
            (A) LENGTH: 42 base pairs
            (B) TYPE: nucleic acid
            (C) STRANDEDNESS: single
            (D) TOPOLOGY: linear (ii) MOLECULE TYPE: Other nucleic acid
            (A) DESCRIPTION: (Mixed DNA/RNA oligomer
                see specification and figures for details)

(xi) SEQUENCE DESCRIPTION: SEQ ID NO:18:

GTCCTAGGCU CUGAUGAGUC CTTTTGGACG AAACUUCCTG GA                            42

(2) INFORMATION FOR SEQ ID NO:19:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:19:

AATTAACCCT CACTA                                                         15

(2) INFORMATION FOR SEQ ID NO:20:

(i) SEQUENCE CHARACTERISTICS:
            (A) LENGTH: 81 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:20:

ACCTGCGGGT TTCAAAATCA TCAGATGAAG TGTCCGAAGA CACTTCATGA CCCGCAGGTA         60

AACCTTTAGT GAGGGTTAAA T                                                  81

(2) INFORMATION FOR SEQ ID NO:21:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: RNA (genomic)

(xi) SEQUENCE DESCRIPTION: SEQ ID NO:21:

GCAUUUCAGU CAGUUGCUCA A                                                  21

(2) INFORMATION FOR SEQ ID NO:22:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:22:

```
GCGGGUCAUG AAG                                                      13
```

(2) INFORMATION FOR SEQ ID NO:23:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:23:

```
GGAAGUCAGC CUA                                                      13
```

(2) INFORMATION FOR SEQ ID NO:24:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: Other nucleic acid
        (A) DESCRIPTION: (Mixed DNA/RNA oligomer
            see specification and figures for details)

(xi) SEQUENCE DESCRIPTION: SEQ ID NO:24:

```
GACACTTCAT CUGAUGAGUC CUUUUGGACG AAACCCGCAG GT                      42
```

(2) INFORMATION FOR SEQ ID NO:25:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:25:

```
ACCUGCGGGU CAUGAAGUGU C                                             21
```

(2) INFORMATION FOR SEQ ID NO:26:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: Other nucleic acid
        (A) DESCRIPTION: (Mixed DNA/RNA oligomer
            see specification and figures for details)

(xi) SEQUENCE DESCRIPTION: SEQ ID NO:26:

```
GTCCTAGGCT CUGAUGAGUC CUUUUGGACG AAACTTCCTG GA                      42
```

(2) INFORMATION FOR SEQ ID NO:27:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:27:

UUCCAGGAAG UCAGCCUAGG AC                                                    22

(2) INFORMATION FOR SEQ ID NO:28:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: Other nucleic acid
        (A) DESCRIPTION: (Mixed DNA/RNA oligomer
            see specification and figures for details)

(xi) SEQUENCE DESCRIPTION: SEQ ID NO:28:

AAGATGATCT CUGAUGAGUC CUUUUGGACG AAACTGCCTG G                               41

(2) INFORMATION FOR SEQ ID NO:29:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:29:

CCAGGCAGUC AGAUCAUCUU                                                       20

(2) INFORMATION FOR SEQ ID NO:30:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: Other nucleic acid
        (A) DESCRIPTION: (Mixed DNA/RNA oligomer
            see specification and figures for details)

(xi) SEQUENCE DESCRIPTION: SEQ ID NO:30:

CAATGCAACU GAUGAGUCCU UUUGGACGAA ACAGGA                                     36

(2) INFORMATION FOR SEQ ID NO:31:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:31:

UCCUGUCUUG CAUUG                                                            15